United States Patent
Fairchild et al.

(10) Patent No.: US 10,869,637 B2
(45) Date of Patent: Dec. 22, 2020

(54) METHOD, SYSTEM, AND COMPUTER READABLE MEDIUM FOR GENERATING PULSE OXIMETRY PREDICTIVE SCORES (POPS) FOR PREDICTING ADVERSE OUTCOMES IN PRETERM INFANTS

(71) Applicant: UNIVERSITY OF VIRGINIA PATENT FOUNDATION, Charlottesville, VA (US)

(72) Inventors: Karen D. Fairchild, Charlottesville, VA (US); Douglas E. Lake, Charlottesville, VA (US); Brynne Sullivan, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 126 days.

(21) Appl. No.: 15/801,226

(22) Filed: Nov. 1, 2017

(65) Prior Publication Data

US 2018/0070886 A1    Mar. 15, 2018

Related U.S. Application Data

(63) Continuation-in-part of application No. PCT/US2017/030606, filed on May 2, 2017.

(60) Provisional application No. 62/330,463, filed on May 2, 2016.

(51) Int. Cl.
*A61B 5/00*  (2006.01)
*A61B 5/1455*  (2006.01)
*G16H 50/30*  (2018.01)
*G16H 15/00*  (2018.01)

(52) U.S. Cl.
CPC .......... *A61B 5/7275* (2013.01); *A61B 5/1455* (2013.01); *A61B 5/14551* (2013.01); *A61B 5/48* (2013.01); *G16H 50/30* (2018.01); *A61B 2503/045* (2013.01); *A61M 2230/205* (2013.01); *G16H 15/00* (2018.01)

(58) Field of Classification Search
None
See application file for complete search history.

(56) References Cited

U.S. PATENT DOCUMENTS

| | | | | |
|---|---|---|---|---|
| 5,285,793 A | * | 2/1994 | Slovut | A61B 5/0468 128/925 |
| 5,596,993 A | * | 1/1997 | Oriol | A61B 5/02411 128/925 |
| 7,734,334 B2 | * | 6/2010 | Mietus | A61B 5/0205 600/513 |
| 9,462,975 B2 | * | 10/2016 | Sackner | A61B 5/6805 |

(Continued)

FOREIGN PATENT DOCUMENTS

WO    2014/205139 A1    12/2014

OTHER PUBLICATIONS

Fairchild et al; "Septicemia Mortality Reduction in Neonates in a Heart Rate Characteristics Monitoring Trial"; Pediatr Res. Author manuscript; available in PMC May 19, 2014; pp. 1-15.

(Continued)

*Primary Examiner* — Carl H Layno
*Assistant Examiner* — Manolis Pahakis
(74) *Attorney, Agent, or Firm* — Potomac Law Group, PLLC; Vincent M DeLuca

(57) ABSTRACT

A method and system for generating pulse oximetry predictive scores for predicting adverse outcomes in preterm infants.

14 Claims, 19 Drawing Sheets

(56) References Cited

U.S. PATENT DOCUMENTS

| | | | |
|---|---|---|---|
| 9,572,511 B2* | 2/2017 | Kochba | A61B 5/0507 |
| 9,839,364 B2* | 12/2017 | Moorman | A61B 5/02405 |
| 2003/0073910 A1* | 4/2003 | Chance | A61B 5/0059 |
| | | | 600/473 |
| 2003/0100841 A1 | 5/2003 | Griffin et al. | |
| 2004/0230105 A1* | 11/2004 | Geva | A61B 5/04012 |
| | | | 600/301 |
| 2005/0010120 A1* | 1/2005 | Jung | A61B 5/044 |
| | | | 600/509 |
| 2006/0235315 A1* | 10/2006 | Akselrod | A61B 5/0456 |
| | | | 600/509 |
| 2007/0031873 A1* | 2/2007 | Wang | C12Q 1/6886 |
| | | | 435/6.14 |
| 2007/0167704 A1* | 7/2007 | Chance | A61B 5/0059 |
| | | | 600/407 |
| 2007/0276270 A1* | 11/2007 | Tran | A61B 5/0022 |
| | | | 600/508 |
| 2009/0036790 A1* | 2/2009 | Landesberg | A61M 16/021 |
| | | | 600/529 |
| 2009/0124867 A1* | 5/2009 | Hirsh | A61M 5/142 |
| | | | 600/301 |
| 2009/0304246 A1* | 12/2009 | Walker | G01S 7/52034 |
| | | | 382/128 |
| 2012/0271372 A1* | 10/2012 | Osorio | A61B 5/7275 |
| | | | 607/17 |
| 2013/0203044 A1 | 8/2013 | Fairchild et al. | |
| 2014/0257128 A1* | 9/2014 | Moxon | A61B 5/0476 |
| | | | 600/544 |
| 2016/0007892 A1* | 1/2016 | Esenaliev | A61B 5/14542 |
| | | | 600/309 |
| 2016/0143594 A1* | 5/2016 | Moorman | A61B 5/02405 |
| | | | 705/2 |
| 2017/0347906 A1* | 12/2017 | Intrator | A61B 5/6803 |
| 2017/0355754 A1* | 12/2017 | Watzlawik | C07K 16/28 |
| 2018/0280646 A1* | 10/2018 | Freeman | A61M 16/024 |

OTHER PUBLICATIONS

Moorman et al; "Mortality Reduction by Heart Rate Characteristic Monitoring in Very Low Birth Weight Neonates: A Randomized Trial"; J Pediatr. Author manuscript; available in PMC Dec. 1, 2012; pp. 1-14.

Belal et al; "Automatic detection of apnoea of prematurity; Automatic detection of AP"; Physiological Measurement, Institute of Physics Publishing, Bristol, GB; vol. 32; No. 5; Mar. 21, 2011; pp. 523-542.

Sola et al: "Safe oxygen saturation targeting and monitoring in preterm infants: can we avoid hypoxia and hyperoxia?"; Acta Paediatrica; Safe oxygen saturation in preterm infants; vol. 103; No. 10; Jul. 28, 2014; pp. 1009-1018.

Tehrani; "A Control System for Oxygen Therapy of Premature Infants"; 2001 Conference Proceedings of the 23rd Annual International Conference of the IEEE Engineering in Medicine and Biology Society (Cat. No. 01CH37272); vol. 3; [Annual International Conference of the IEEE Engineering in Medicine and Biology Society. EMBS]; vol. 2, Oct. 25, 2001; pp. 2059-2062.

* cited by examiner

| OUTCOME | n= | GA WKS (MEAN, SD) | BW GRAMS (MEAN, SD) | <3h SpO$_2$ % (MEAN, SD) |
|---|---|---|---|---|
| DIED ≤3D | 17 | 29 ± 4 | 1288 ± 635 | 78 ± 16* |
| DIED >3D | 18 | 27 ± 4 | 1078 ± 740 | 93 ± 4 |
| SURVIVED | 895 | 31 ± 3 | 1620 ± 584 | 95 ± 4** |
| TRANSFERRED | 48 | 30 ± 3 | 1343 ± 548 | 95 ± 3 |
| DISCHARGED HOME ≤40W PMA >40W PMA | 771 76 | 31 ± 3 27 ± 3 | 1705 ± 547 931 ± 457 | 95 ± 4† 92 ± 9 |

*P<0.01 VS. LATE DEATH; **P<0.01 VS. ALL DEATH, †P<0.01 VS. LATE DISCHARGE

| CATEGORY | VARIABLE | MEASURE | ALL MEAN (SD) | EVENT MEAN (SD) | ROC AREA† | P= | VS + PMA ROC AREA* | P= |
|---|---|---|---|---|---|---|---|---|
| VITAL SIGNS | HEART RATE | MEAN | 158 (12) | 161 (13) | 0.551 | 0.003 | 0.707 | 0.182 |
| | RESP. RATE | | 51 (11) | 50 (12) | 0.540 | 0.174 | 0.701 | 0.243 |
| | SpO$_2$% | | 94 (4) | 91 (5) | 0.634 | 0.000 | 0.718 | 0.000 |
| | HEART RATE | STD. DEV. | 7 (3) | 6 (3) | 0.596 | 0.000 | 0.706 | 0.121 |
| | RESP. RATE | | 17 (5) | 17 (6) | 0.530 | 0.054 | 0.701 | 0.365 |
| | SpO$_2$% | | 3 (2) | 4 (3) | 0.594 | 0.000 | 0.714 | 0.000 |
| | HR-RR | CROSS-CORRELATION | 0.15 (0.09) | 0.18 (0.12) | 0.579 | 0.000 | 0.722 | 0.000 |
| | HR-SpO$_2$ | | 0.10 (0.16) | 0.21 (0.22) | 0.652 | 0.000 | 0.733 | 0.000 |
| | RR-SpO$_2$ | | 0.23 (0.12) | 0.25 (0.13) | 0.527 | 0.091 | 0.699 | 0.137 |
| DEMOGRAPHIC | BWT | GRAMS | 920 (288) | 817 (261) | 0.605 | 0.000 | 0.715 | 0.00 |
| | GA | WEEKS | 26.8 (2.6) | 25.9 (2.5) | 0.604 | 0.000 | 0.707 | 0.03 |
| | PMA | WEEKS | 34.1 (6.4) | 30.4 (4.3) | 0.705 | 0.000 | NA | NA |
| | MALE | % | 54% | 55% | 0.503 | 0.860 | 0.705 | 0.79 |

NICU=NEONATAL INTENSIVE CARE UNIT; LOS=LATE-ONSET SEPTICEMIA;
NEC=NECROTIZING ENTEROCOLITIS; HR=HEART RATE; RR=RESPIRATORY RATE;
SD=STD.DEV.=STANDARD DEVIATION; ROC=RECEIVER OPERATOR CHARACTERISTICS CURVE;
MAX.=MAXIMUM; BWT=BIRTH WEIGHT; GA=GESTATIONAL AGE; PMA=POSTMENSTRUAL AGE

†ROC AREA COMPARING 0-24H PRIOR TO LOS OR NEC DIAGNOSIS TO ALL DATA.
*BIVARIATE ANALYSIS

*FIG. 3*

| VITAL SIGN* | UVA CHI-SQUARED | P= | CU CHI-SQUARED | P= | COMBINED CHI-SQUARED | P= |
|---|---|---|---|---|---|---|
| MEAN HEART RATE | 7.201 | 0.0073 | 0.881 | 0.3479 | 3.198 | 0.0737 |
| MEAN RESP. RATE | 6.104 | 0.0135 | 15.242 | 0.0001 | 18.439 | 0.0000 |
| MEAN SpO₂ % | 20.826 | 0.0000 | 0.547 | 0.4596 | 24.974 | 0.0000 |
| SD HR | 17.971 | 0.0000 | 30.885 | 0.0000 | 38.675 | 0.0000 |
| SD RR | 4.491 | 0.0341 | 11.830 | 0.0006 | 13.615 | 0.0002 |
| SD SpO₂ | 0.475 | 0.4906 | 8.159 | 0.0043 | 0.199 | 0.6558 |
| XC HR-RR | 7.404 | 0.0065 | 3.420 | 0.0644 | 9.023 | 0.0027 |
| XC HR-SpO₂ | 36.487 | 0.0000 | 36.530 | 0.0000 | 73.957 | 0.0000 |
| XC RR-SpO₂ | 0.650 | 0.4203 | 8.522 | 0.0035 | 0.946 | 0.3307 |

| MODEL | ROC AREA | 95% CI | ROC AREA | 95% CI | ROC AREA | 95% CI |
|---|---|---|---|---|---|---|
| 9-VARIABLE MODEL | 0.711 | 0.674-0.734 | 0.770 | 0.727-0.812 | 0.721 | 0.691-0.743 |
| 3-VARIABLE MODEL ** | 0.695 | 0.654-0.721 | 0.745 | 0.710-0.786 | 0.710 | 0.679-0.728 |
| XC HR-SpO₂ | 0.617 | 0.577-0.651 | 0.701 | 0.654-0.752 | 0.644 | 0.618-0.673 |

*CONTRIBUTION TO THE 9-VARIABLE MODEL
**MEAN SpO₂, SD HR, AND XC HR-SpO₂
XC CROSS CORRELATION; HR HEART RATE; RR RESPIRATORY RATE

*FIG. 4*

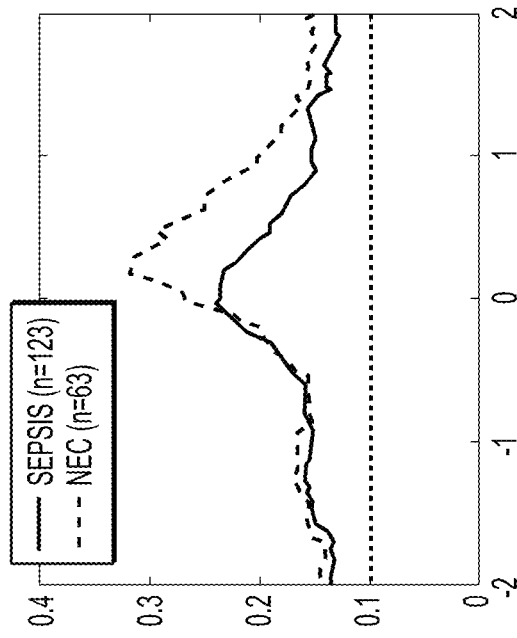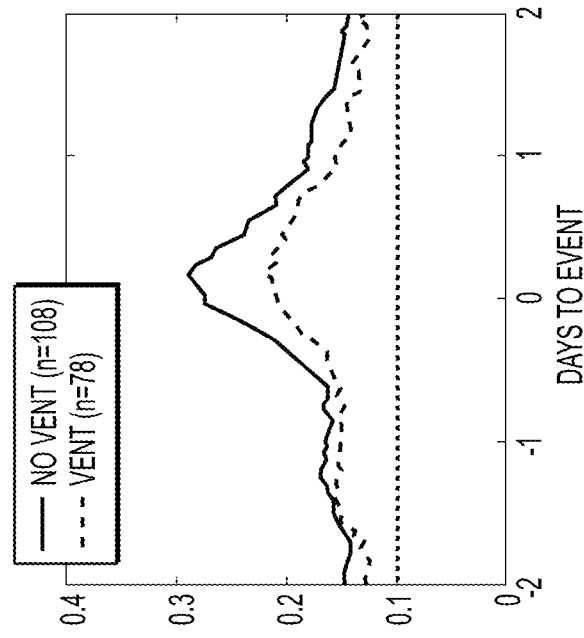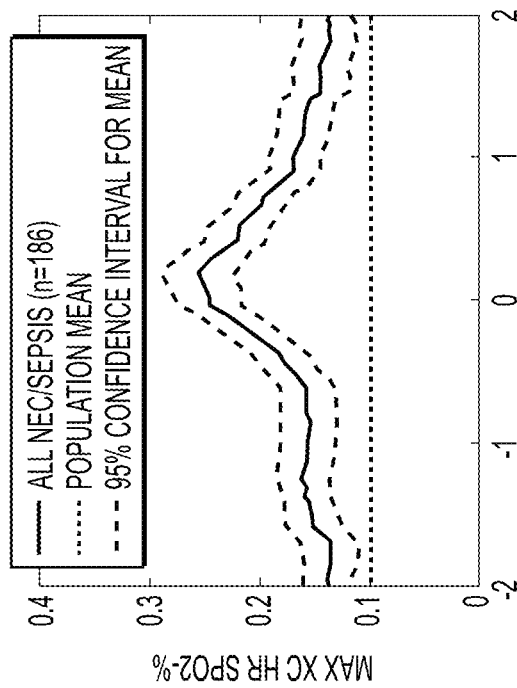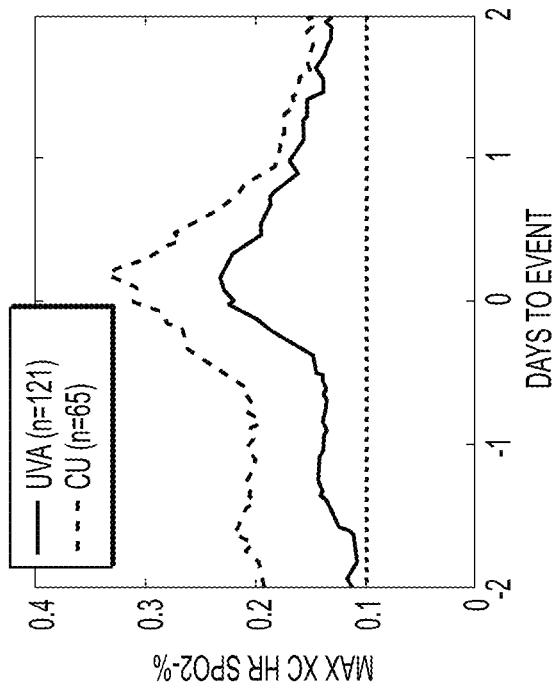
FIG. 5

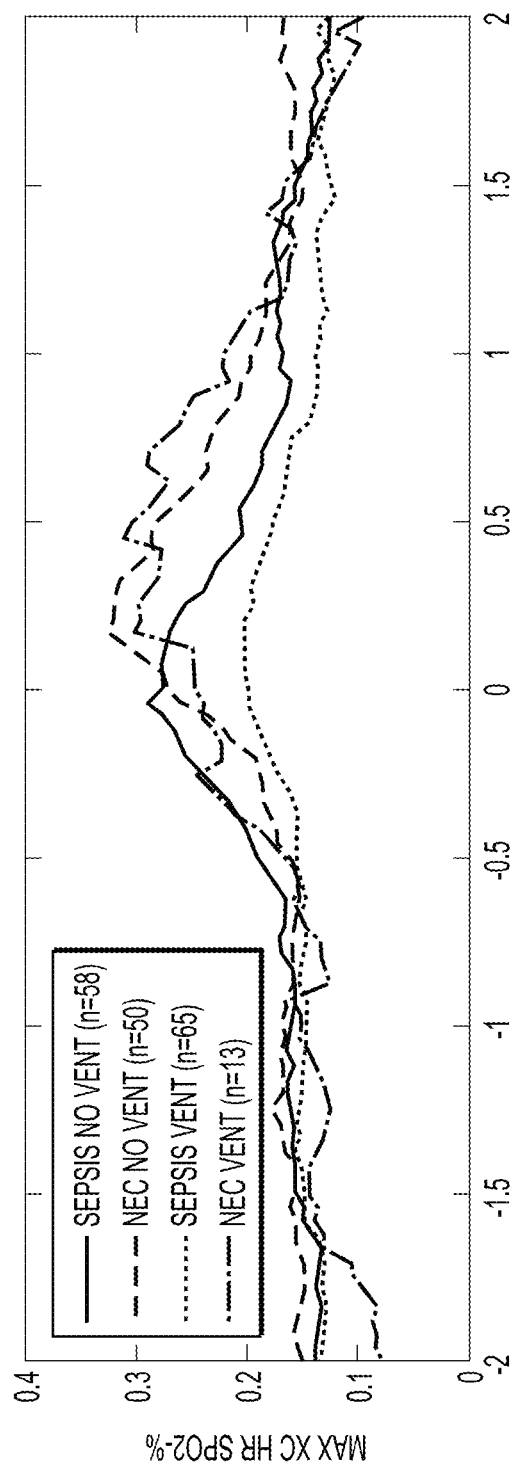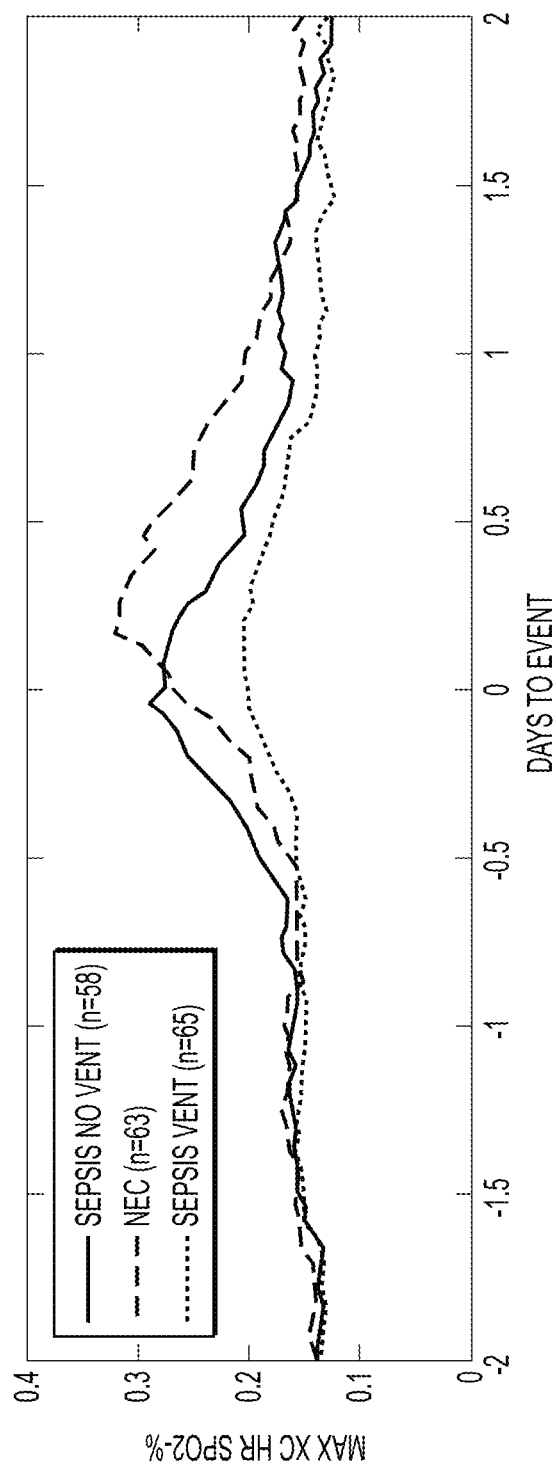
FIG. 8

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| -7.00 | 0.15 | 0.06 | 0.07 | 0.17 | 0.15 | 0.07 | 0.07 |
| -6.96 | 0.13 | 0.07 | 0.06 | 0.11 | 0.13 | 0.08 | 0.06 |
| -6.92 | 0.13 | 0.07 | 0.07 | 0.09 | 0.13 | 0.07 | 0.07 |
| -6.88 | 0.13 | 0.06 | 0.08 | 0.04 | 0.13 | 0.06 | 0.08 |
| -6.83 | 0.13 | 0.06 | 0.09 | 0.04 | 0.13 | 0.06 | 0.09 |
| -6.79 | 0.14 | 0.06 | 0.09 | 0.05 | 0.14 | 0.06 | 0.09 |
| -6.75 | 0.14 | 0.07 | 0.10 | 0.07 | 0.14 | 0.07 | 0.10 |
| -6.71 | 0.15 | 0.06 | 0.10 | 0.07 | 0.15 | 0.07 | 0.10 |
| -6.67 | 0.15 | 0.07 | 0.11 | 0.09 | 0.15 | 0.07 | 0.11 |
| -6.63 | 0.15 | 0.07 | 0.11 | 0.09 | 0.15 | 0.07 | 0.11 |
| -6.58 | 0.15 | 0.06 | 0.11 | 0.10 | 0.15 | 0.07 | 0.11 |
| -6.54 | 0.15 | 0.06 | 0.11 | 0.09 | 0.15 | 0.07 | 0.11 |
| -6.50 | 0.15 | 0.07 | 0.11 | 0.09 | 0.15 | 0.07 | 0.11 |
| -6.46 | 0.15 | 0.07 | 0.11 | 0.10 | 0.15 | 0.08 | 0.11 |
| -6.42 | 0.15 | 0.07 | 0.11 | 0.11 | 0.15 | 0.08 | 0.11 |
| -6.38 | 0.15 | 0.08 | 0.11 | 0.11 | 0.15 | 0.09 | 0.11 |
| -6.33 | 0.15 | 0.09 | 0.11 | 0.12 | 0.15 | 0.09 | 0.11 |
| -6.29 | 0.14 | 0.09 | 0.11 | 0.11 | 0.14 | 0.09 | 0.11 |
| -6.25 | 0.14 | 0.09 | 0.10 | 0.10 | 0.14 | 0.09 | 0.10 |
| -6.21 | 0.13 | 0.09 | 0.10 | 0.09 | 0.13 | 0.09 | 0.10 |
| -6.17 | 0.13 | 0.09 | 0.10 | 0.09 | 0.13 | 0.09 | 0.10 |
| -6.13 | 0.14 | 0.10 | 0.09 | 0.10 | 0.14 | 0.10 | 0.09 |
| -6.08 | 0.13 | 0.11 | 0.09 | 0.10 | 0.13 | 0.11 | 0.09 |
| -6.04 | 0.13 | 0.11 | 0.10 | 0.10 | 0.13 | 0.10 | 0.10 |
| -6.00 | 0.11 | 0.11 | 0.09 | 0.10 | 0.11 | 0.11 | 0.09 |
| -5.96 | 0.11 | 0.11 | 0.10 | 0.10 | 0.11 | 0.11 | 0.10 |
| -5.92 | 0.11 | 0.11 | 0.11 | 0.11 | 0.11 | 0.11 | 0.11 |
| -5.88 | 0.11 | 0.11 | 0.11 | 0.12 | 0.11 | 0.11 | 0.11 |
| -5.83 | 0.11 | 0.11 | 0.11 | 0.13 | 0.11 | 0.11 | 0.11 |
| -5.79 | 0.11 | 0.11 | 0.11 | 0.14 | 0.11 | 0.11 | 0.11 |
| -5.75 | 0.11 | 0.12 | 0.11 | 0.13 | 0.11 | 0.12 | 0.11 |
| -5.71 | 0.11 | 0.11 | 0.11 | 0.14 | 0.11 | 0.12 | 0.11 |
| -5.67 | 0.13 | 0.11 | 0.11 | 0.17 | 0.13 | 0.12 | 0.11 |
| -5.63 | 0.13 | 0.11 | 0.11 | 0.15 | 0.13 | 0.12 | 0.11 |
| -5.58 | 0.12 | 0.12 | 0.10 | 0.14 | 0.12 | 0.12 | 0.10 |
| -5.54 | 0.12 | 0.12 | 0.11 | 0.14 | 0.12 | 0.12 | 0.11 |
| -5.50 | 0.12 | 0.11 | 0.10 | 0.13 | 0.12 | 0.11 | 0.10 |
| -5.46 | 0.12 | 0.11 | 0.10 | 0.12 | 0.12 | 0.11 | 0.10 |
| -5.42 | 0.12 | 0.11 | 0.11 | 0.11 | 0.12 | 0.11 | 0.11 |
| -5.38 | 0.12 | 0.11 | 0.10 | 0.11 | 0.12 | 0.11 | 0.10 |
| -5.33 | 0.12 | 0.11 | 0.10 | 0.10 | 0.12 | 0.11 | 0.10 |
| -5.29 | 0.11 | 0.11 | 0.11 | 0.10 | 0.11 | 0.11 | 0.11 |
| -5.25 | 0.10 | 0.11 | 0.11 | 0.10 | 0.10 | 0.11 | 0.11 |
| -5.21 | 0.10 | 0.10 | 0.12 | 0.09 | 0.10 | 0.10 | 0.12 |
| -5.17 | 0.10 | 0.12 | 0.11 | 0.09 | 0.10 | 0.11 | 0.11 |
| -5.13 | 0.10 | 0.11 | 0.11 | 0.09 | 0.10 | 0.11 | 0.11 |

*FIG. 9A*

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| -5.08 | 0.11 | 0.11 | 0.11 | 0.09 | 0.11 | 0.11 | 0.11 |
| -5.04 | 0.11 | 0.11 | 0.12 | 0.09 | 0.11 | 0.11 | 0.12 |
| -5.00 | 0.13 | 0.11 | 0.12 | 0.11 | 0.13 | 0.11 | 0.12 |
| -4.96 | 0.14 | 0.10 | 0.12 | 0.11 | 0.14 | 0.10 | 0.12 |
| -4.92 | 0.14 | 0.10 | 0.12 | 0.13 | 0.14 | 0.10 | 0.12 |
| -4.88 | 0.13 | 0.10 | 0.13 | 0.14 | 0.13 | 0.11 | 0.13 |
| -4.83 | 0.13 | 0.10 | 0.12 | 0.15 | 0.13 | 0.10 | 0.12 |
| -4.79 | 0.13 | 0.10 | 0.13 | 0.16 | 0.13 | 0.11 | 0.13 |
| -4.75 | 0.14 | 0.10 | 0.13 | 0.16 | 0.14 | 0.11 | 0.13 |
| -4.71 | 0.14 | 0.10 | 0.12 | 0.16 | 0.14 | 0.11 | 0.12 |
| -4.67 | 0.14 | 0.10 | 0.13 | 0.17 | 0.14 | 0.11 | 0.13 |
| -4.63 | 0.14 | 0.10 | 0.14 | 0.17 | 0.14 | 0.11 | 0.14 |
| -4.58 | 0.14 | 0.10 | 0.14 | 0.16 | 0.14 | 0.11 | 0.14 |
| -4.54 | 0.13 | 0.11 | 0.13 | 0.15 | 0.13 | 0.11 | 0.13 |
| -4.50 | 0.13 | 0.12 | 0.13 | 0.14 | 0.13 | 0.13 | 0.13 |
| -4.46 | 0.13 | 0.12 | 0.12 | 0.14 | 0.13 | 0.12 | 0.12 |
| -4.42 | 0.13 | 0.12 | 0.11 | 0.12 | 0.13 | 0.12 | 0.11 |
| -4.38 | 0.13 | 0.12 | 0.11 | 0.12 | 0.13 | 0.12 | 0.11 |
| -4.33 | 0.13 | 0.12 | 0.11 | 0.12 | 0.13 | 0.12 | 0.11 |
| -4.29 | 0.13 | 0.11 | 0.11 | 0.12 | 0.13 | 0.11 | 0.11 |
| -4.25 | 0.13 | 0.11 | 0.10 | 0.10 | 0.13 | 0.11 | 0.10 |
| -4.21 | 0.14 | 0.11 | 0.10 | 0.10 | 0.14 | 0.11 | 0.10 |
| -4.17 | 0.14 | 0.11 | 0.10 | 0.09 | 0.14 | 0.10 | 0.10 |
| -4.13 | 0.14 | 0.11 | 0.10 | 0.09 | 0.14 | 0.11 | 0.10 |
| -4.08 | 0.14 | 0.11 | 0.10 | 0.08 | 0.14 | 0.10 | 0.10 |
| -4.04 | 0.14 | 0.11 | 0.09 | 0.08 | 0.14 | 0.10 | 0.09 |
| -4.00 | 0.13 | 0.11 | 0.09 | 0.08 | 0.13 | 0.10 | 0.09 |
| -3.96 | 0.12 | 0.11 | 0.09 | 0.09 | 0.12 | 0.11 | 0.09 |
| -3.92 | 0.12 | 0.11 | 0.10 | 0.11 | 0.12 | 0.11 | 0.10 |
| -3.88 | 0.12 | 0.11 | 0.10 | 0.11 | 0.12 | 0.11 | 0.10 |
| -3.83 | 0.12 | 0.12 | 0.11 | 0.10 | 0.12 | 0.12 | 0.11 |
| -3.79 | 0.13 | 0.12 | 0.11 | 0.10 | 0.13 | 0.12 | 0.11 |
| -3.75 | 0.13 | 0.11 | 0.11 | 0.09 | 0.13 | 0.11 | 0.11 |
| -3.71 | 0.13 | 0.12 | 0.11 | 0.10 | 0.13 | 0.11 | 0.11 |
| -3.67 | 0.13 | 0.12 | 0.11 | 0.10 | 0.13 | 0.12 | 0.11 |
| -3.63 | 0.13 | 0.12 | 0.11 | 0.10 | 0.13 | 0.11 | 0.11 |
| -3.58 | 0.13 | 0.12 | 0.11 | 0.11 | 0.13 | 0.12 | 0.11 |
| -3.54 | 0.13 | 0.12 | 0.12 | 0.12 | 0.13 | 0.12 | 0.11 |
| -3.50 | 0.13 | 0.12 | 0.12 | 0.11 | 0.13 | 0.12 | 0.12 |
| -3.46 | 0.13 | 0.13 | 0.12 | 0.09 | 0.13 | 0.12 | 0.12 |
| -3.42 | 0.13 | 0.13 | 0.12 | 0.09 | 0.13 | 0.12 | 0.12 |
| -3.38 | 0.13 | 0.13 | 0.12 | 0.09 | 0.13 | 0.12 | 0.12 |
| -3.33 | 0.12 | 0.12 | 0.12 | 0.11 | 0.12 | 0.12 | 0.12 |
| -3.29 | 0.13 | 0.11 | 0.13 | 0.12 | 0.13 | 0.11 | 0.13 |
| -3.25 | 0.13 | 0.11 | 0.13 | 0.14 | 0.13 | 0.12 | 0.13 |
| -3.21 | 0.12 | 0.11 | 0.12 | 0.13 | 0.12 | 0.11 | 0.12 |

*FIG. 9B*

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| -3.17 | 0.12 | 0.11 | 0.12 | 0.13 | 0.12 | 0.11 | 0.12 |
| -3.13 | 0.13 | 0.12 | 0.12 | 0.12 | 0.13 | 0.12 | 0.12 |
| -3.08 | 0.13 | 0.12 | 0.12 | 0.10 | 0.13 | 0.12 | 0.12 |
| -3.04 | 0.13 | 0.12 | 0.11 | 0.09 | 0.13 | 0.12 | 0.11 |
| -3.00 | 0.13 | 0.12 | 0.11 | 0.08 | 0.13 | 0.12 | 0.11 |
| -2.96 | 0.13 | 0.12 | 0.11 | 0.08 | 0.13 | 0.12 | 0.11 |
| -2.92 | 0.13 | 0.12 | 0.11 | 0.07 | 0.13 | 0.11 | 0.11 |
| -2.88 | 0.13 | 0.12 | 0.11 | 0.08 | 0.13 | 0.11 | 0.11 |
| -2.83 | 0.13 | 0.12 | 0.11 | 0.07 | 0.13 | 0.11 | 0.11 |
| -2.79 | 0.13 | 0.13 | 0.11 | 0.07 | 0.13 | 0.12 | 0.11 |
| -2.75 | 0.14 | 0.12 | 0.12 | 0.06 | 0.14 | 0.11 | 0.12 |
| -2.71 | 0.14 | 0.12 | 0.11 | 0.06 | 0.14 | 0.11 | 0.11 |
| -2.67 | 0.15 | 0.11 | 0.11 | 0.06 | 0.15 | 0.11 | 0.11 |
| -2.63 | 0.15 | 0.12 | 0.11 | 0.08 | 0.15 | 0.11 | 0.11 |
| -2.58 | 0.15 | 0.12 | 0.11 | 0.11 | 0.15 | 0.12 | 0.11 |
| -2.54 | 0.14 | 0.13 | 0.12 | 0.12 | 0.14 | 0.13 | 0.12 |
| -2.50 | 0.13 | 0.13 | 0.12 | 0.12 | 0.13 | 0.13 | 0.12 |
| -2.46 | 0.13 | 0.13 | 0.13 | 0.13 | 0.13 | 0.13 | 0.13 |
| -2.42 | 0.13 | 0.13 | 0.13 | 0.12 | 0.13 | 0.13 | 0.13 |
| -2.38 | 0.13 | 0.13 | 0.13 | 0.11 | 0.13 | 0.13 | 0.13 |
| -2.33 | 0.14 | 0.13 | 0.14 | 0.12 | 0.14 | 0.13 | 0.14 |
| -2.29 | 0.14 | 0.13 | 0.14 | 0.11 | 0.14 | 0.13 | 0.14 |
| -2.25 | 0.13 | 0.14 | 0.14 | 0.10 | 0.13 | 0.13 | 0.14 |
| -2.21 | 0.14 | 0.14 | 0.15 | 0.11 | 0.14 | 0.14 | 0.15 |
| -2.17 | 0.13 | 0.15 | 0.15 | 0.12 | 0.13 | 0.14 | 0.15 |
| -2.13 | 0.13 | 0.15 | 0.15 | 0.11 | 0.13 | 0.14 | 0.15 |
| -2.08 | 0.13 | 0.15 | 0.14 | 0.09 | 0.13 | 0.14 | 0.14 |
| -2.04 | 0.13 | 0.15 | 0.14 | 0.08 | 0.13 | 0.14 | 0.14 |
| -2.00 | 0.14 | 0.15 | 0.13 | 0.08 | 0.14 | 0.14 | 0.13 |
| -1.96 | 0.14 | 0.16 | 0.13 | 0.09 | 0.14 | 0.14 | 0.13 |
| -1.92 | 0.14 | 0.16 | 0.13 | 0.09 | 0.14 | 0.15 | 0.13 |
| -1.88 | 0.13 | 0.16 | 0.13 | 0.09 | 0.13 | 0.14 | 0.13 |
| -1.83 | 0.13 | 0.15 | 0.13 | 0.08 | 0.13 | 0.14 | 0.13 |
| -1.79 | 0.13 | 0.15 | 0.13 | 0.09 | 0.13 | 0.14 | 0.13 |
| -1.75 | 0.13 | 0.15 | 0.14 | 0.11 | 0.13 | 0.14 | 0.14 |
| -1.71 | 0.13 | 0.15 | 0.13 | 0.11 | 0.13 | 0.14 | 0.13 |
| -1.67 | 0.13 | 0.16 | 0.14 | 0.13 | 0.13 | 0.15 | 0.14 |
| -1.63 | 0.14 | 0.16 | 0.14 | 0.13 | 0.14 | 0.15 | 0.14 |
| -1.58 | 0.15 | 0.16 | 0.15 | 0.14 | 0.15 | 0.15 | 0.15 |
| -1.54 | 0.15 | 0.16 | 0.15 | 0.14 | 0.15 | 0.16 | 0.15 |
| -1.50 | 0.15 | 0.16 | 0.15 | 0.14 | 0.15 | 0.16 | 0.15 |
| -1.46 | 0.16 | 0.16 | 0.15 | 0.15 | 0.16 | 0.16 | 0.15 |
| -1.42 | 0.15 | 0.16 | 0.15 | 0.15 | 0.15 | 0.16 | 0.15 |
| -1.38 | 0.16 | 0.17 | 0.16 | 0.14 | 0.16 | 0.16 | 0.16 |
| -1.33 | 0.16 | 0.17 | 0.15 | 0.13 | 0.16 | 0.16 | 0.15 |
| -1.29 | 0.16 | 0.17 | 0.16 | 0.13 | 0.16 | 0.17 | 0.16 |

*FIG. 9C*

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| -1.25 | 0.16 | 0.18 | 0.16 | 0.13 | 0.16 | 0.17 | 0.16 |
| -1.21 | 0.16 | 0.17 | 0.15 | 0.13 | 0.16 | 0.17 | 0.15 |
| -1.17 | 0.16 | 0.17 | 0.15 | 0.13 | 0.16 | 0.17 | 0.15 |
| -1.13 | 0.16 | 0.17 | 0.15 | 0.14 | 0.16 | 0.16 | 0.15 |
| -1.08 | 0.16 | 0.17 | 0.15 | 0.14 | 0.16 | 0.17 | 0.15 |
| -1.04 | 0.16 | 0.17 | 0.15 | 0.16 | 0.16 | 0.16 | 0.15 |
| -1.00 | 0.16 | 0.17 | 0.15 | 0.15 | 0.16 | 0.17 | 0.15 |
| -0.96 | 0.16 | 0.17 | 0.15 | 0.16 | 0.16 | 0.16 | 0.15 |
| -0.92 | 0.16 | 0.17 | 0.15 | 0.16 | 0.16 | 0.17 | 0.15 |
| -0.88 | 0.16 | 0.16 | 0.15 | 0.13 | 0.16 | 0.15 | 0.15 |
| -0.83 | 0.16 | 0.16 | 0.15 | 0.13 | 0.16 | 0.15 | 0.15 |
| -0.79 | 0.17 | 0.16 | 0.15 | 0.14 | 0.17 | 0.16 | 0.15 |
| -0.75 | 0.17 | 0.16 | 0.15 | 0.14 | 0.17 | 0.16 | 0.15 |
| -0.71 | 0.17 | 0.16 | 0.15 | 0.15 | 0.17 | 0.16 | 0.15 |
| -0.67 | 0.17 | 0.16 | 0.15 | 0.16 | 0.17 | 0.16 | 0.15 |
| -0.63 | 0.16 | 0.16 | 0.15 | 0.16 | 0.16 | 0.16 | 0.15 |
| -0.58 | 0.17 | 0.15 | 0.15 | 0.15 | 0.17 | 0.15 | 0.15 |
| -0.54 | 0.18 | 0.15 | 0.15 | 0.16 | 0.18 | 0.16 | 0.15 |
| -0.50 | 0.19 | 0.17 | 0.16 | 0.17 | 0.19 | 0.17 | 0.16 |
| -0.46 | 0.19 | 0.17 | 0.16 | 0.18 | 0.19 | 0.17 | 0.16 |
| -0.42 | 0.20 | 0.18 | 0.16 | 0.19 | 0.20 | 0.18 | 0.16 |
| -0.38 | 0.21 | 0.18 | 0.16 | 0.21 | 0.21 | 0.19 | 0.16 |
| -0.33 | 0.22 | 0.19 | 0.16 | 0.22 | 0.22 | 0.19 | 0.16 |
| -0.29 | 0.23 | 0.19 | 0.17 | 0.24 | 0.23 | 0.19 | 0.17 |
| -0.25 | 0.24 | 0.19 | 0.17 | 0.25 | 0.24 | 0.20 | 0.17 |
| -0.21 | 0.25 | 0.19 | 0.18 | 0.22 | 0.25 | 0.20 | 0.18 |
| -0.17 | 0.26 | 0.21 | 0.19 | 0.22 | 0.26 | 0.21 | 0.19 |
| -0.13 | 0.27 | 0.22 | 0.19 | 0.23 | 0.27 | 0.22 | 0.19 |
| -0.08 | 0.28 | 0.23 | 0.20 | 0.24 | 0.28 | 0.24 | 0.20 |
| -0.04 | 0.29 | 0.26 | 0.20 | 0.24 | 0.29 | 0.26 | 0.20 |
| 0.00 | 0.28 | 0.27 | 0.20 | 0.25 | 0.28 | 0.27 | 0.20 |
| 0.04 | 0.27 | 0.28 | 0.20 | 0.25 | 0.27 | 0.27 | 0.20 |
| 0.08 | 0.28 | 0.29 | 0.20 | 0.25 | 0.28 | 0.28 | 0.20 |
| 0.13 | 0.27 | 0.31 | 0.20 | 0.25 | 0.27 | 0.29 | 0.20 |
| 0.17 | 0.27 | 0.32 | 0.20 | 0.30 | 0.27 | 0.32 | 0.20 |
| 0.21 | 0.26 | 0.32 | 0.20 | 0.30 | 0.26 | 0.32 | 0.20 |
| 0.25 | 0.25 | 0.32 | 0.20 | 0.30 | 0.25 | 0.32 | 0.20 |
| 0.29 | 0.24 | 0.32 | 0.20 | 0.29 | 0.24 | 0.31 | 0.20 |
| 0.33 | 0.23 | 0.31 | 0.20 | 0.28 | 0.23 | 0.31 | 0.20 |
| 0.38 | 0.23 | 0.30 | 0.19 | 0.28 | 0.23 | 0.29 | 0.19 |
| 0.42 | 0.22 | 0.29 | 0.19 | 0.28 | 0.22 | 0.28 | 0.19 |
| 0.46 | 0.20 | 0.29 | 0.18 | 0.31 | 0.20 | 0.29 | 0.18 |
| 0.50 | 0.21 | 0.28 | 0.18 | 0.30 | 0.21 | 0.29 | 0.18 |
| 0.54 | 0.21 | 0.27 | 0.17 | 0.29 | 0.21 | 0.27 | 0.17 |
| 0.58 | 0.20 | 0.26 | 0.17 | 0.28 | 0.20 | 0.26 | 0.17 |
| 0.63 | 0.19 | 0.24 | 0.17 | 0.27 | 0.19 | 0.25 | 0.17 |

FIG. 9D

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| 0.67 | 0.19 | 0.24 | 0.17 | 0.29 | 0.19 | 0.25 | 0.17 |
| 0.71 | 0.18 | 0.24 | 0.16 | 0.29 | 0.18 | 0.25 | 0.16 |
| 0.75 | 0.18 | 0.23 | 0.16 | 0.27 | 0.18 | 0.24 | 0.16 |
| 0.79 | 0.17 | 0.23 | 0.15 | 0.26 | 0.17 | 0.24 | 0.15 |
| 0.83 | 0.16 | 0.22 | 0.14 | 0.26 | 0.16 | 0.23 | 0.14 |
| 0.88 | 0.16 | 0.21 | 0.14 | 0.25 | 0.16 | 0.22 | 0.14 |
| 0.92 | 0.16 | 0.20 | 0.14 | 0.22 | 0.16 | 0.21 | 0.14 |
| 0.96 | 0.17 | 0.20 | 0.14 | 0.22 | 0.17 | 0.20 | 0.14 |
| 1.00 | 0.17 | 0.20 | 0.14 | 0.22 | 0.17 | 0.20 | 0.14 |
| 1.04 | 0.17 | 0.19 | 0.14 | 0.21 | 0.17 | 0.19 | 0.14 |
| 1.08 | 0.17 | 0.19 | 0.14 | 0.21 | 0.17 | 0.19 | 0.14 |
| 1.13 | 0.17 | 0.18 | 0.13 | 0.20 | 0.17 | 0.19 | 0.13 |
| 1.17 | 0.17 | 0.18 | 0.13 | 0.17 | 0.17 | 0.18 | 0.13 |
| 1.21 | 0.17 | 0.18 | 0.14 | 0.16 | 0.17 | 0.18 | 0.14 |
| 1.25 | 0.17 | 0.18 | 0.14 | 0.16 | 0.17 | 0.17 | 0.14 |
| 1.29 | 0.17 | 0.17 | 0.14 | 0.16 | 0.17 | 0.17 | 0.14 |
| 1.33 | 0.18 | 0.16 | 0.14 | 0.16 | 0.18 | 0.16 | 0.14 |
| 1.38 | 0.17 | 0.16 | 0.14 | 0.16 | 0.17 | 0.16 | 0.14 |
| 1.42 | 0.17 | 0.16 | 0.13 | 0.19 | 0.17 | 0.17 | 0.13 |
| 1.46 | 0.16 | 0.15 | 0.12 | 0.17 | 0.16 | 0.16 | 0.12 |
| 1.50 | 0.16 | 0.15 | 0.13 | 0.17 | 0.16 | 0.16 | 0.13 |
| 1.54 | 0.15 | 0.16 | 0.13 | 0.16 | 0.15 | 0.16 | 0.13 |
| 1.58 | 0.14 | 0.16 | 0.13 | 0.14 | 0.14 | 0.16 | 0.13 |
| 1.63 | 0.15 | 0.16 | 0.14 | 0.14 | 0.15 | 0.16 | 0.14 |
| 1.67 | 0.14 | 0.16 | 0.14 | 0.14 | 0.14 | 0.16 | 0.14 |
| 1.71 | 0.14 | 0.16 | 0.13 | 0.13 | 0.14 | 0.15 | 0.13 |
| 1.75 | 0.14 | 0.16 | 0.13 | 0.13 | 0.14 | 0.15 | 0.13 |
| 1.79 | 0.14 | 0.16 | 0.13 | 0.12 | 0.14 | 0.15 | 0.13 |
| 1.83 | 0.13 | 0.16 | 0.12 | 0.11 | 0.13 | 0.15 | 0.12 |
| 1.88 | 0.14 | 0.17 | 0.13 | 0.11 | 0.14 | 0.15 | 0.13 |
| 1.92 | 0.13 | 0.17 | 0.13 | 0.10 | 0.13 | 0.15 | 0.13 |
| 1.96 | 0.12 | 0.17 | 0.14 | 0.12 | 0.12 | 0.16 | 0.14 |
| 2.00 | 0.13 | 0.17 | 0.13 | 0.10 | 0.13 | 0.15 | 0.13 |
| 2.04 | 0.13 | 0.17 | 0.13 | 0.10 | 0.13 | 0.15 | 0.13 |
| 2.08 | 0.13 | 0.16 | 0.12 | 0.11 | 0.13 | 0.14 | 0.12 |
| 2.13 | 0.13 | 0.16 | 0.11 | 0.10 | 0.13 | 0.14 | 0.11 |
| 2.17 | 0.13 | 0.16 | 0.12 | 0.08 | 0.13 | 0.14 | 0.12 |
| 2.21 | 0.13 | 0.16 | 0.11 | 0.08 | 0.13 | 0.14 | 0.11 |
| 2.25 | 0.13 | 0.16 | 0.11 | 0.08 | 0.13 | 0.14 | 0.11 |
| 2.29 | 0.13 | 0.15 | 0.11 | 0.09 | 0.13 | 0.13 | 0.11 |
| 2.33 | 0.12 | 0.14 | 0.11 | 0.10 | 0.12 | 0.13 | 0.11 |
| 2.38 | 0.13 | 0.13 | 0.11 | 0.10 | 0.13 | 0.13 | 0.11 |
| 2.42 | 0.13 | 0.13 | 0.11 | 0.11 | 0.13 | 0.13 | 0.11 |
| 2.46 | 0.12 | 0.13 | 0.10 | 0.10 | 0.12 | 0.13 | 0.10 |
| 2.50 | 0.13 | 0.13 | 0.10 | 0.11 | 0.13 | 0.12 | 0.10 |
| 2.54 | 0.13 | 0.13 | 0.10 | 0.11 | 0.13 | 0.12 | 0.10 |

*FIG. 9E*

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| 2.58 | 0.14 | 0.13 | 0.10 | 0.11 | 0.14 | 0.13 | 0.10 |
| 2.63 | 0.14 | 0.13 | 0.10 | 0.13 | 0.14 | 0.13 | 0.10 |
| 2.67 | 0.14 | 0.13 | 0.10 | 0.13 | 0.14 | 0.13 | 0.10 |
| 2.71 | 0.13 | 0.12 | 0.11 | 0.13 | 0.13 | 0.12 | 0.11 |
| 2.75 | 0.13 | 0.13 | 0.11 | 0.15 | 0.13 | 0.13 | 0.11 |
| 2.79 | 0.13 | 0.13 | 0.11 | 0.15 | 0.13 | 0.13 | 0.11 |
| 2.83 | 0.13 | 0.12 | 0.11 | 0.14 | 0.13 | 0.13 | 0.11 |
| 2.88 | 0.13 | 0.13 | 0.11 | 0.15 | 0.13 | 0.13 | 0.11 |
| 2.92 | 0.13 | 0.12 | 0.11 | 0.16 | 0.13 | 0.13 | 0.11 |
| 2.96 | 0.14 | 0.12 | 0.11 | 0.16 | 0.14 | 0.13 | 0.11 |
| 3.00 | 0.14 | 0.12 | 0.11 | 0.17 | 0.14 | 0.13 | 0.11 |
| 3.04 | 0.13 | 0.12 | 0.11 | 0.17 | 0.13 | 0.13 | 0.11 |
| 3.08 | 0.13 | 0.11 | 0.11 | 0.18 | 0.13 | 0.13 | 0.11 |
| 3.13 | 0.13 | 0.11 | 0.11 | 0.18 | 0.13 | 0.12 | 0.11 |
| 3.17 | 0.12 | 0.11 | 0.12 | 0.19 | 0.12 | 0.13 | 0.12 |
| 3.21 | 0.13 | 0.11 | 0.12 | 0.18 | 0.13 | 0.12 | 0.12 |
| 3.25 | 0.13 | 0.10 | 0.12 | 0.14 | 0.13 | 0.11 | 0.12 |
| 3.29 | 0.14 | 0.10 | 0.12 | 0.14 | 0.14 | 0.11 | 0.12 |
| 3.33 | 0.14 | 0.10 | 0.13 | 0.14 | 0.14 | 0.11 | 0.13 |
| 3.38 | 0.14 | 0.10 | 0.13 | 0.14 | 0.14 | 0.11 | 0.13 |
| 3.42 | 0.14 | 0.11 | 0.14 | 0.14 | 0.14 | 0.11 | 0.14 |
| 3.46 | 0.13 | 0.10 | 0.14 | 0.15 | 0.13 | 0.11 | 0.14 |
| 3.50 | 0.14 | 0.09 | 0.14 | 0.15 | 0.14 | 0.11 | 0.14 |
| 3.54 | 0.14 | 0.10 | 0.14 | 0.15 | 0.14 | 0.11 | 0.14 |
| 3.58 | 0.14 | 0.10 | 0.14 | 0.17 | 0.14 | 0.12 | 0.14 |
| 3.63 | 0.14 | 0.10 | 0.14 | 0.15 | 0.14 | 0.11 | 0.14 |
| 3.67 | 0.14 | 0.10 | 0.14 | 0.17 | 0.14 | 0.11 | 0.14 |
| 3.71 | 0.14 | 0.10 | 0.15 | 0.19 | 0.14 | 0.12 | 0.15 |
| 3.75 | 0.14 | 0.10 | 0.14 | 0.17 | 0.14 | 0.12 | 0.14 |
| 3.79 | 0.13 | 0.11 | 0.15 | 0.18 | 0.13 | 0.12 | 0.15 |
| 3.83 | 0.12 | 0.11 | 0.14 | 0.18 | 0.12 | 0.12 | 0.14 |
| 3.88 | 0.12 | 0.11 | 0.14 | 0.17 | 0.12 | 0.12 | 0.14 |
| 3.92 | 0.13 | 0.11 | 0.14 | 0.18 | 0.13 | 0.13 | 0.14 |
| 3.96 | 0.13 | 0.12 | 0.14 | 0.15 | 0.13 | 0.13 | 0.14 |
| 4.00 | 0.13 | 0.13 | 0.14 | 0.15 | 0.13 | 0.13 | 0.14 |
| 4.04 | 0.13 | 0.13 | 0.14 | 0.14 | 0.13 | 0.13 | 0.14 |
| 4.08 | 0.13 | 0.13 | 0.14 | 0.14 | 0.13 | 0.13 | 0.14 |
| 4.13 | 0.14 | 0.12 | 0.13 | 0.13 | 0.14 | 0.12 | 0.13 |
| 4.17 | 0.14 | 0.12 | 0.13 | 0.13 | 0.14 | 0.12 | 0.13 |
| 4.21 | 0.14 | 0.11 | 0.13 | 0.12 | 0.14 | 0.12 | 0.13 |
| 4.25 | 0.14 | 0.12 | 0.13 | 0.14 | 0.14 | 0.12 | 0.13 |
| 4.29 | 0.14 | 0.12 | 0.13 | 0.14 | 0.14 | 0.12 | 0.13 |
| 4.33 | 0.14 | 0.13 | 0.13 | 0.13 | 0.14 | 0.13 | 0.13 |
| 4.38 | 0.13 | 0.14 | 0.13 | 0.14 | 0.13 | 0.14 | 0.13 |
| 4.42 | 0.14 | 0.14 | 0.13 | 0.14 | 0.14 | 0.14 | 0.13 |
| 4.46 | 0.13 | 0.14 | 0.13 | 0.14 | 0.13 | 0.14 | 0.13 |

*FIG. 9F*

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| 4.50 | 0.13 | 0.15 | 0.13 | 0.14 | 0.13 | 0.15 | 0.13 |
| 4.54 | 0.13 | 0.15 | 0.13 | 0.14 | 0.13 | 0.15 | 0.13 |
| 4.58 | 0.14 | 0.14 | 0.13 | 0.14 | 0.14 | 0.14 | 0.13 |
| 4.63 | 0.13 | 0.14 | 0.13 | 0.11 | 0.13 | 0.14 | 0.13 |
| 4.67 | 0.13 | 0.14 | 0.13 | 0.09 | 0.13 | 0.13 | 0.13 |
| 4.71 | 0.12 | 0.13 | 0.13 | 0.11 | 0.12 | 0.13 | 0.13 |
| 4.75 | 0.12 | 0.12 | 0.13 | 0.11 | 0.12 | 0.12 | 0.13 |
| 4.79 | 0.12 | 0.13 | 0.13 | 0.11 | 0.12 | 0.12 | 0.13 |
| 4.83 | 0.12 | 0.12 | 0.13 | 0.11 | 0.12 | 0.12 | 0.13 |
| 4.88 | 0.12 | 0.11 | 0.13 | 0.11 | 0.12 | 0.11 | 0.13 |
| 4.92 | 0.13 | 0.11 | 0.13 | 0.11 | 0.13 | 0.11 | 0.13 |
| 4.96 | 0.13 | 0.11 | 0.14 | 0.11 | 0.13 | 0.11 | 0.14 |
| 5.00 | 0.13 | 0.10 | 0.13 | 0.11 | 0.13 | 0.10 | 0.13 |
| 5.04 | 0.13 | 0.10 | 0.13 | 0.14 | 0.13 | 0.11 | 0.13 |
| 5.08 | 0.13 | 0.10 | 0.13 | 0.15 | 0.13 | 0.11 | 0.13 |
| 5.13 | 0.14 | 0.10 | 0.13 | 0.15 | 0.14 | 0.11 | 0.13 |
| 5.17 | 0.13 | 0.10 | 0.12 | 0.14 | 0.13 | 0.11 | 0.12 |
| 5.21 | 0.14 | 0.10 | 0.12 | 0.15 | 0.14 | 0.11 | 0.12 |
| 5.25 | 0.14 | 0.11 | 0.13 | 0.15 | 0.14 | 0.11 | 0.13 |
| 5.29 | 0.14 | 0.11 | 0.13 | 0.16 | 0.14 | 0.12 | 0.13 |
| 5.33 | 0.14 | 0.11 | 0.13 | 0.16 | 0.14 | 0.12 | 0.13 |
| 5.38 | 0.14 | 0.12 | 0.13 | 0.16 | 0.14 | 0.13 | 0.13 |
| 5.42 | 0.13 | 0.12 | 0.13 | 0.17 | 0.13 | 0.13 | 0.13 |
| 5.46 | 0.12 | 0.12 | 0.13 | 0.16 | 0.12 | 0.13 | 0.13 |
| 5.50 | 0.12 | 0.13 | 0.13 | 0.17 | 0.12 | 0.13 | 0.13 |
| 5.54 | 0.12 | 0.12 | 0.13 | 0.14 | 0.12 | 0.13 | 0.13 |
| 5.58 | 0.12 | 0.12 | 0.13 | 0.13 | 0.12 | 0.12 | 0.13 |
| 5.63 | 0.12 | 0.12 | 0.13 | 0.13 | 0.12 | 0.12 | 0.13 |
| 5.67 | 0.12 | 0.12 | 0.13 | 0.14 | 0.12 | 0.13 | 0.13 |
| 5.71 | 0.12 | 0.12 | 0.12 | 0.15 | 0.12 | 0.13 | 0.12 |
| 5.75 | 0.12 | 0.12 | 0.14 | 0.16 | 0.12 | 0.13 | 0.14 |
| 5.79 | 0.12 | 0.11 | 0.14 | 0.16 | 0.12 | 0.12 | 0.14 |
| 5.83 | 0.12 | 0.11 | 0.13 | 0.15 | 0.12 | 0.12 | 0.13 |
| 5.88 | 0.11 | 0.11 | 0.13 | 0.14 | 0.11 | 0.12 | 0.13 |
| 5.92 | 0.12 | 0.11 | 0.13 | 0.14 | 0.12 | 0.12 | 0.13 |
| 5.96 | 0.12 | 0.11 | 0.13 | 0.15 | 0.12 | 0.12 | 0.13 |
| 6.00 | 0.12 | 0.11 | 0.13 | 0.19 | 0.12 | 0.12 | 0.13 |
| 6.04 | 0.11 | 0.10 | 0.13 | 0.18 | 0.11 | 0.12 | 0.13 |
| 6.08 | 0.11 | 0.10 | 0.13 | 0.18 | 0.11 | 0.12 | 0.13 |
| 6.13 | 0.11 | 0.10 | 0.13 | 0.17 | 0.11 | 0.12 | 0.13 |
| 6.17 | 0.12 | 0.09 | 0.13 | 0.17 | 0.12 | 0.11 | 0.13 |
| 6.21 | 0.11 | 0.09 | 0.12 | 0.16 | 0.11 | 0.10 | 0.12 |
| 6.25 | 0.11 | 0.09 | 0.13 | 0.15 | 0.11 | 0.10 | 0.13 |
| 6.29 | 0.10 | 0.09 | 0.12 | 0.14 | 0.10 | 0.10 | 0.12 |
| 6.33 | 0.11 | 0.08 | 0.11 | 0.16 | 0.11 | 0.10 | 0.11 |
| 6.38 | 0.11 | 0.08 | 0.11 | 0.16 | 0.11 | 0.09 | 0.11 |

*FIG. 9G*

| DAYS TO EVENT | SEPSIS NO VENT | NEC NO VENT | SEPSIS VENT | NEC VENT | SEPSIS NO VENT | NEC | SEPSIS VENT |
|---|---|---|---|---|---|---|---|
| 6.42 | 0.11 | 0.07 | 0.12 | 0.16 | 0.11 | 0.09 | 0.12 |
| 6.46 | 0.11 | 0.07 | 0.11 | 0.15 | 0.11 | 0.09 | 0.11 |
| 6.50 | 0.10 | 0.08 | 0.12 | 0.13 | 0.10 | 0.09 | 0.12 |
| 6.54 | 0.10 | 0.08 | 0.11 | 0.10 | 0.10 | 0.08 | 0.11 |
| 6.58 | 0.11 | 0.09 | 0.11 | 0.16 | 0.11 | 0.10 | 0.11 |
| 6.63 | 0.11 | 0.09 | 0.11 | 0.17 | 0.11 | 0.11 | 0.11 |
| 6.67 | 0.10 | 0.10 | 0.11 | 0.18 | 0.10 | 0.11 | 0.11 |
| 6.71 | 0.11 | 0.10 | 0.11 | 0.21 | 0.11 | 0.13 | 0.11 |
| 6.75 | 0.11 | 0.11 | 0.11 | 0.22 | 0.11 | 0.13 | 0.11 |
| 6.79 | 0.11 | 0.11 | 0.11 | 0.23 | 0.11 | 0.14 | 0.11 |
| 6.83 | 0.11 | 0.11 | 0.11 | 0.23 | 0.11 | 0.14 | 0.11 |
| 6.88 | 0.11 | 0.11 | 0.11 | 0.23 | 0.11 | 0.14 | 0.11 |
| 6.92 | 0.10 | 0.12 | 0.11 | 0.26 | 0.10 | 0.15 | 0.11 |
| 6.96 | 0.11 | 0.13 | 0.11 | 0.26 | 0.11 | 0.15 | 0.11 |
| 7.00 | 0.11 | 0.13 | 0.11 | 0.26 | 0.11 | 0.16 | 0.11 |

METHOD, SYSTEM, AND COMPUTER READABLE MEDIUM FOR GENERATING PULSE OXIMETRY PREDICTIVE SCORES (POPS) FOR PREDICTING ADVERSE OUTCOMES IN PRETERM INFANTS

RELATED APPLICATION

This is a Continuation-In-Part (CIP) application of PCT Application No. PCT/US17/30606, filed on May 2, 2017, which claims the benefit of U.S. Provisional Application No. 62/330,463, filed on May 2, 2016.

GOVERNMENT SUPPORT CLAUSE

This invention was made with government support under Grant No. HD072071 awarded by the National Institutes of Health. The government has certain rights in the invention.

FIELD

The present invention is directed to a method, system, and computer readable medium for generating pulse oximetry predictive scores for predicting adverse outcomes in preterm infants.

BACKGROUND

Pulse oximetry is universally used to monitor all infants in the Neonatal Intensive Care Unit (NICU), from birth until discharge. There is an abundance of important physiologic information in the pulse oximetry signal, and clinicians use only a fraction of this data. Abnormal patterns of heart rate or oxygenation can indicate risk for adverse events or outcomes occurring in the near or far term.

There exists a need for generating pulse oximetry predictive scores (POPS) for predicting adverse outcomes in preterm infants. The pulse oximetry predictive scores (POPS) can be used to: 1) identify highest-risk infants for additional surveillance or therapeutic interventions that might not be appropriate for all preterm infants; 2) stratify infants for clinical trials based on risk profiles; 3) provide early warning system for late-onset sepsis and necrotizing enterocolitis (NEC); and 4) earlier diagnosis and treatment to improve outcomes.

SUMMARY

The presently described subject matter is directed to an improved method, system, and apparatus for pulse oximetry predictive scores for predicting adverse outcomes in preterm infants.

The presently described subject matter is directed to a method for generating pulse oximetry predictive scores for predicting adverse outcomes in preterm infants, comprising or consisting of a predictive algorithm.

The presently described subject matter is directed to a method for generating pulse oximetry predictive scores for predicting adverse outcomes in preterm infants, comprising or consisting essentially of or consisting of a predictive algorithm; and displaying the resulting predictive scores.

The presently described subject matter is directed to a method for generating pulse oximetry predictive scores for predicting adverse outcomes in preterm infants, comprising or consisting essentially of or consisting of: measuring mean and standard deviation of heart rate (HR) and oxygen saturation (SpO2); measuring cross-correlation of HR and SpO2; measuring HR decelerations; measuring HR and SpO2 entropy; measuring hypoxia and hyperoxia; analyzing the measured data; and generating pulse oximetry predictive scores using the analyzed data, wherein these measurements are made over different time periods specific to a pathology being predicted.

The presently described subject matter is directed to the above method for pulse oximetry predictive scores for predicting adverse outcomes in preterm infants, wherein the time periods are based on death or intraventricular hemorrhage (IVH) at first 24 hour or shorter time periods, after birth.

The presently described subject matter is directed to the above method for pulse oximetry predictive scores for predicting adverse outcomes in preterm infants, wherein the time periods are based on sepsis or NEC at 2 days leading up to clinical diagnosis, including increase over patient baseline or increase over population normal.

The presently described subject matter is directed to the above method for pulse oximetry predictive scores for predicting adverse outcomes in preterm infants, wherein the time periods are based on bronchopulmonary dysplasia (BPD) or retinopathy of prematurity (ROP) at first day, week, or month.

The presently described subject matter is directed to the above method for pulse oximetry predictive scores for predicting adverse outcomes in preterm infants, wherein the time periods are based on prolonged Neonatal Intensive Care Unit (NICU) stay at first day, week, or month.

The presently described subject matter is directed to the above method for pulse oximetry predictive scores for predicting adverse outcomes in preterm infants, including generating an algorithm using gestational age, birth weight, and post-menstrual age.

The presently described subject matter is directed to the above method for pulse oximetry predictive scores for predicting adverse outcomes in preterm infants, including exploring specific laboratory values, including white blood cell count, hematocrit, and C-reactive protein.

The presently described subject matter is directed to the above method for pulse oximetry predictive scores for predicting adverse outcomes in preterm infants, including developing predictive scores using pulse oximeter-derived heart rate (HR) and oxygen saturation (SpO2).

The presently described subject matter is directed to the above method for pulse oximetry predictive scores for predicting adverse outcomes in preterm infants, including developing predictive scores using pulse oximeter-derived heart rate (HR) and oxygen saturation (SpO2), and including using standard demographic risk factors to determine risk of early or late death or prolonged NICU stay.

The presently described subject matter is directed to the above method for pulse oximetry predictive scores for predicting adverse outcomes in preterm infants, including monitoring changes in cardiorespiratory changes occurring in the preterm infants with systemic inflammation related to late-onset septicemia (LOS) or necrotizing enterocolitis (NEC), and alerting clinicians before overt signs of illness emerges.

The presently described subject matter is directed to the above method for pulse oximetry predictive scores for predicting adverse outcomes in preterm infants, including monitoring changes in cardiorespiratory changes occurring in the preterm infants with systemic inflammation related to late-onset septicemia (LOS) or necrotizing enterocolitis (NEC), and alerting clinicians before overt signs of illness emerges, and further including monitoring respiratory rate (RR), heart rate (HR), and oxygen saturation (SpO2) of the preterm infants.

The presently described subject matter is directed to the above method for pulse oximetry predictive scores for predicting adverse outcomes in preterm infants, including monitoring changes in vital sign patterns of the preterm infants.

The presently described subject matter is directed to the above method for pulse oximetry predictive scores for predicting adverse outcomes in preterm infants, including monitoring changes in vital sign patterns of the preterm infants, wherein the monitoring data, includes respiration rate (RR) is derived from the chest impedance signal, heart rate (HR) is derived from an electrocardiogram (ECG) signal, and SpO2 is derived from a pulse oximeter, and the monitoring data is collected every 2 seconds.

The presently described subject matter is directed to the above method for pulse oximetry predictive scores for predicting adverse outcomes in preterm infants, including monitoring changes in vital sign patterns of the preterm infants, wherein the monitoring data, includes respiration rate (RR) is derived from the chest impedance signal, heart rate (HR) is derived from an electrocardiogram (ECG) signal, and SpO2 is derived from a pulse oximeter, and the monitoring data is collected every 2 seconds and further wherein maximum cross-correlation between two vital sign signals is measured over ten-minute windows by first standardizing each signal and then using a Matlab function XCORR, with a lag time of −30 to +30 seconds.

BRIEF DESCRIPTION OF DRAWINGS

FIG. 3 is a table of vital signs and their cross-correlation over the entire NICU stay and in the $24^{th}$ period prior to LOS or NEC events.

FIG. 4 is a table of site-specific vital sign and model performance for LOS and NEC detection.

FIG. 5 show graphs of center-specific vital sign model ability to discriminate infants with impending LOS or NEC.

FIG. 8 show graphs of the effect as seen in infants at both institutions.

FIGS. 9A-H show tables of effect in infants on or off mechanical ventilation at the time of diagnosis.

FIG. 12 is a diagram illustrating Heart Rate and Oxygen Saturation Cross-Correlation in Preterm Infants: Association with Apnea and Adverse Events.

DETAILED DESCRIPTION OF PREFERRED EMBODIMENTS

Figures 1, 2:
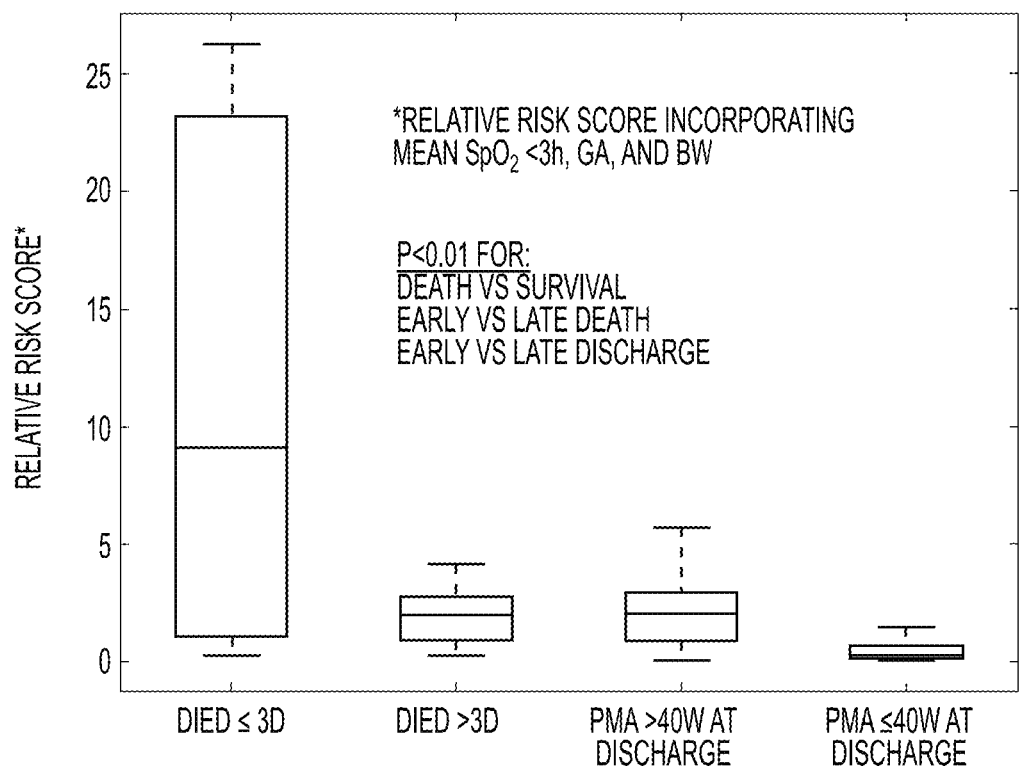
FIG. 1 is a table of pulse oximetry data showing death rates.
FIG. 2 is a diagrammatic view showing the relative risk score for various time periods.

The present invention is directed to a method, system, and computer readable medium for generating pulse oximetry predictive scores for predicting adverse outcomes in preterm infants.

The pulse oximetry predictive scores (POPS) can be used to: 1) identify highest-risk infants for additional surveillance or therapeutic interventions that might not be appropriate for all preterm infants; 2) stratify infants for clinical trials based on risk profiles; 3) provide early warning system for late-onset sepsis and NEC; and 4) earlier diagnosis and treatment to improve outcomes.

The present invention includes:
1) analyzing archived pulse oximetry data and carefully annotated and audited clinical data from ~1000 preterm infants in the UVA NICU from 2009-2015; and
2) developing pulse oximetry-based algorithms to predict:
   a) death (early <3 days or late >=3 days);
   b) intraventricular hemorrhage (this generally occurs within the first 3 days after birth, is associated with adverse neurodevelopmental outcomes);
   c) sepsis (early <3 days or late >=3 days blood culture-positive sepsis);
   d) necrotizing enterocolitis (NEC);
   e) bronchopulmonary dysplasia (BPD) or chronic lung disease which is associated with prolonged length of NICU stay and long-term respiratory and neurologic morbidity);
   f) retinopathy of prematurity (ROP, retinal vasculopathy with risk for blindness); and
   g) prolonged NICU stay (which is costly).

The measurements according to the present invention include:
   a) mean and standard deviation of HR and SpO2;
   b) cross-correlation of HR and SpO2;
   c) HR decelerations;
   d) HR and SpO2 entropy; and
   e) hypoxia and hyperoxia measurements including hypoxia index (area under curve of various SpO2 thresholds, 88%, 85%, 80%, 75%), number of hypoxia or hyperoxia events, "delta SpO2" or depth and frequency of acute decrease/increase in SpO2.

These measurements will be made over different time periods specific to the pathology being predicted. For example:
   1) death or IVH in first 24 hour or shorter time period after birth;
   2) sepsis or NEC in 2 days leading up to clinical diagnosis (increase over patient baseline or increase over population normal);
   3) BPD or ROP in first day, week, month. For both, it is possible that hyperoxia and hypoxia have time windows of susceptibility to organ damage, which will be evaluated; and
   4) prolonged NICU stay in first day, week, or month.

The present invention can determine the additive value of variables such as gestational age, birth weight, and post-menstrual age into the algorithms.

The present invention can explore the additive value of specific laboratory values (or changes in laboratory values) such as white blood cell count, hematocrit, C-reactive protein.

The present invention can advise on methodology, including both basic modeling (e.g. logistic regression models) and methods such as random forest, decision tree, machine learning.

The present invention includes analysis of archived data at both University of Virginia (UVA) and Columbia University (CU) for model development, and alternative training/testing data sets to assure models work across institutions. The present invention can include a third NICU with high-volume/high acuity to develop and validate the models.

The pulse oximetry predictive scores (POPS) can be used to:
1) identify highest-risk infants for additional surveillance or therapeutic interventions that might not be appropriate for all preterm infants;
2) stratify infants for clinical trials based on risk profiles; and
3) provide an early warning method or system for late-onset sepsis and NEC to provide earlier diagnosis and treatment likely leading to improved outcomes.

The bedside display of pulse oximetry predictive scores (POPS) can facilitate the early detection of sepsis/NEC. Further, the pulse oximetry data within 3 hours of birth can be used to predict death and prolonged NICU stays for preterm infants. In addition, predicting adverse events in preterm infants is useful for risk stratification in clinical trials and quality improvement initiatives.

To develop pulse oximetry predictive scores (POPS) using pulse oximeter-derived heart rate (HR) and oxygen saturation (SpO2) from the day of birth can add to standard demographic risk factors to determine relative risk of early or late death or prolonged NICU stay.

For all infants <35 weeks gestational age (GA) admitted at birth to the UVA NICU from 2009-2015, pulse oximeter data was analyzed within 3 hrs of birth. The relative risk of mortality was estimated using a parsimonious logistic regression model with variables of gestational age (GA), birth weight (BW), and mean SpO2 obtained using a stepwise selection process. In a separate analysis using random forests, significant variables identified in order of importance included mean SPO2, percent SPO2<85, BW, standard deviation of SPO2, percent SPO2<80, and standard deviation of HR.

The score generated from this model was evaluated for discriminating adverse outcomes including early ("3 d) and late (>3 d) death and prolonged NICU stay (beyond 40 week post-menstrual age).

Pulse oximetry data was available in the first 3 hours after birth for 930 infants, of which 35 died, as shown in FIG. 1). Mean SpO2 added significantly to gestational age (GA) and birth weight (BW) to predict overall mortality (AUC 0.850, change in AUC 0.146, p<0.0001). The relative risk score predicted early compared to late death and prolonged NICU stay, as shown in FIG. 2.

The average oxygen saturation (SpO2) obtained from pulse oximetry in the first 3 hours after birth predicts early and late death and older postmenstrual age at discharge in preterm infants and adds to the gestational age and birth weight for risk prediction.

Cardiorespiratory changes occur in preterm infants with systemic inflammation related to late-onset septicemia (LOS) or necrotizing enterocolitis (NEC), and alerting clinicians to these changes before overt signs of illness emerge can lead to earlier treatments and improved outcomes.

Identifying changes in vital signs and their cross-correlation prior to LOS or NEC diagnosis in very low birth weight (VLBW) infants was conducted in two Neonatal Intensive Care Units (NICUs). The analysis of bedside monitor cardiorespiratory and clinical data was used.

The NICUs at the University of Virginia and Columbia University Medical Center. The participants include 1065 preterm very low birth weight (VLBW) infants.

The respiratory rate (RR), heart rate (HR), and oxygen saturation (SpO2) were collected every 2 seconds from the bedside monitors for the entire NICU stay (131 infant-years' data). The mean, standard deviation (SD), and cross-correlation of the vital signs over 10 minute windows averaged each hour were analyzed at all times that data was available resulting in 1.15M measurements, including within 1 day of 186 episodes of LOS or NEC. The vital sign and demographic models were evaluated for ability to predict illness within 24 hours, and the results were compared to heart rate characteristics index previously validated for sepsis detection.

The cross-correlation of HR-SpO2 was the best single measure for either LOS or NEC detection and remained highly significant (p<0.00001) when adjusted for postmenstrual age which was the best demographic predictor (combined ROC area 0.733). A 3-variable model (cross correlation of HR-SpO2, mean SpO2, and SD HR) increased the ROC area by 0.021 over an established heart rate characteristics index for illness prediction (Net Reclassification Improvement 0.25, 95% CI 0.113, 0.328). The model performance differed between the two (2) NICUs, but remained highly significant when internally and externally validated. The 3-variable model trained at UVA had an internal ROC area of 0.695 and an external ROC area of 0.754. The same model trained at Columbia had internal and external ROC areas of 0.745 and 0.680, respectively.

Despite minor inter-institutional differences in vital sign patterns of VLBW infants, cross-correlation of HR-SpO2 and a 3-variable vital sign model performed well at both centers for preclinical detection of sepsis or NEC.

The analysis of changes in vital sign patterns in hospitalized patients can yield important information about impending clinical deterioration and might alert clinicians before they would otherwise recognize signs of illness (See Lake D E, Fairchild K D, Moorman J R. Complex signals bioinformatics: evaluation of heart rate characteristics monitoring as a novel risk marker for neonatal sepsis. J Clin Monit Comput 2013; 28:329-39; Mithal L B, Yogev R, Palac H, Gur I, Mestan K K. Computerized vital signs analysis and late onset infections in extremely low gestational age infants. J Perinat Med 2016; and Bravi A, Green G, Longtin A A, Seely A J E. Monitoring and Identification of Sepsis Development through a Composite Measure of Heart Rate Variability. PLoS One 2012; 7:e45666).

The present inventors previously developed a system for analyzing heart rate characteristics in infants in the neonatal intensive care unit (NICU) that identifies decreased heart rate variability and decelerations that occur prior to diagnosis of sepsis (See Moorman J R, Carlo W A, Kattwinkel J, et al. Mortality reduction by heart rate characteristic monitoring in very low birth weight neonates: A randomized trial. J Pediatr 2011; 159; Griffin M P, O'Shea T M, Bissonette E A, Harrell F E, Lake D E, Moorman J R, Abnormal heart rate characteristics preceding neonatal sepsis and sepsis-like illness. Pediatr Res 2003; 53:920-6; and Griffin M P, Lake D E, Bissonette E A, Harrell F E, O'Shea T M, Moorman J R, Heart rate characteristics: novel physiomarkers to predict neonatal infection and death. Pediatrics 2005; 116:1070-4).

The displaying a heart rate characteristics score to clinicians lowered sepsis-associated mortality 40% in a large randomized clinical trial of very low birth weight (VLBW) infants (See Fairchild K D, Schelonka R L, Kaufman D a, et al. Septicemia mortality reduction in neonates in a heart rate characteristics monitoring trial. Pediatr Res 2013; 74:570-5). While changes in heart rate patterns provide some information about cardiovascular stability and autonomic nervous system activation and dysfunction, changes in other vital signs that occur during a systemic inflammatory response can be exploited for predictive monitoring (See Fairchild K D. Predictive monitoring for early detection of sepsis in neonatal ICU patients. Curr Opin Pediatr 2013; 25:172-9; and Sullivan B A, Fairchild K D. Predictive monitoring for sepsis and necrotizing enterocolitis to prevent shock. Semin Fetal Neonatal Med 2015; 20:255-61).

The acute illness in preterm infants is often associated with increased frequency or severity of central apnea associated with bradycardia and oxygen desaturation ("ABD" events). The present invention can use an automated algorithm that analyzes waveform and vital sign data from NICU bedside monitors to show that ABD events and periodic breathing increase in the day prior to diagnosis in some infants with septicemia or necrotizing enterocolitis (NEC) (See Patel M, Mohr M, Lake D, et al. Clinical Associations with Immature Breathing in Preterm Infants. Part 2: Periodic Breathing. Pediatr Res 2016; and Fairchild K, Mohr M, Paget-Brown A, et al. Clinical associations of immature breathing in preterm infants: part 1-central apnea. Pediatr Res 2016). Waveform data are generally sampled at high frequency by standard ICU monitors (in our units, chest impedance at 60 Hz and 3 leads of ECG at 240 Hz each), and therefore analysis of central apnea requires very large data storage and processing capabilities not available at most centers.

The present invention sought to develop simpler methods for analyzing vital sign values and their interactions to predict acute illness. The present invention focused on vital signs collected every 2 seconds (0.5 Hz) from bedside monitors: heart rate (HR), respiratory rate (RR), and oxygen saturation from pulse oximetry (SpO2). In a preliminary analysis of infants in a single NICU, it was found that increased cross-correlation (or trending together, allowing for a lag) of HR and SpO2 performed well for preclinical detection of sepsis (Moss, Fairchild, Lake, Moorman accepted for publication, Critical Care Medicine, March 2016). Some of this increased cross-correlation likely represents changes in HR and SpO2 occurring in synchrony with pauses in breathing.

In the present invention, the study was expanded on this finding by analyzing vital signs from a large number of VLBW infants in two NICUs, both at baseline and surrounding two illnesses, late-onset septicemia (LOS) and NEC.

The present invention collected and stored all bedside monitor vital sign data on all patients admitted to the University of Virginia (UVA) NICU over a 64 month period from 2009 to 2015 and to the Children's Hospital of New York NICU (Columbia University, CU) over an 18 month period from 2013 to 2015. All VLBW infants with data available were included in this study, which was approved by the Institutional Review Boards of both institutions with waiver of consent due to its purely observational nature.

The clinical data was abstracted from electronic medical records into a relational clinical database. The demographics included gestational age, birth weight, gender, and final outcome (death, discharge, or transfer). The cases of LOS and NEC were identified from review of clinical databases. LOS was defined as signs of sepsis and a positive blood culture at 3 or more days of age and at least 5 days of treatment with antibiotics. The subsequent episodes of LOS or NEC were included if they occurred more than 7 days after the previous episode. NEC is defined as clinical and radiographic signs of NEC and a full course of therapy (bowel rest and antibiotics). The present invention excluded cases of focal intestinal perforation without NEC as identified by the attending neonatologist and pediatric surgeon, based on clinical and, when available, surgical findings. The cases in which infants were transferred from an outside hospital with LOS or NEC were excluded since baseline "well" data were not available for comparison.

The data collected related to LOS or NEC episodes included chronologic and post-menstrual age at the time of the blood culture or abdominal radiograph establishing the diagnosis, blood culture results, and whether on ventilatory support at the time of diagnosis.

The bedside monitor data was collected using a BedMaster central network server (Excel Medical, Jupiter, Fla.). RR derived from the chest impedance signal, HR from the ECG signal, and SpO2 from the pulse oximeter were collected every 2 seconds. During the time period of study at both institutions, pulse oximeters were set to the default SpO2 averaging setting (8 seconds). The mean, standard deviation, and cross-correlation of HR, RR, and SpO2 were calculated in 10 minute windows and then averaged for each hour for analysis throughout the NICU stay and then specifically in the 2 day period before and after diagnosis of LOS and NEC.

The maximum cross-correlation between two vital sign signals was measured over ten-minute windows by first standardizing each signal (subtracting mean and dividing by standard deviation) and then using the Matlab function XCORR, with a lag time of −30 to +30 seconds. A high value of this statistic (approaching 1) indicates the two signals are in positive synchrony (i.e. they go up and down together) with a possible lag or time difference of up to 30 seconds. The present inventors also calculated the minimum cross-correlation value reflecting signals going in opposite directions; these negative synchrony values are not reported because they were not associated with adverse events.

At UVA, a heart rate characteristics (HRC) index monitor has been in use since 2003 (HeRO monitor, Medical Predictive Science Corporation, Charlottesville, Va.). The monitor was developed as an early warning system for sepsis, and the HRC index incorporates three measures of abnormal HR characteristics that occur in some neonates with sepsis: low HR variability, sample asymmetry (more decelerations, fewer accelerations), and low sample entropy. The HRC index is displayed at UVA and not at Columbia, and the present invention compared vital sign metrics examined in this study with the HRC index in UVA patients only.

The summary statistics and logistic regression were used to describe and compare vital signs collected from infants at UVA and Columbia. Univariate logistic regression analyses were performed to determine whether there was a significant change in each vital sign metric in the 24 hour period before diagnosis of LOS or NEC, compared to normative data from all VLBW infants at all times. Demographic variables potentially associated with LOS and NEC (gestational age, birthweight, gender, and postmenstrual age) were also analyzed. Bivariate analyses incorporating postmenstrual age and each vital sign metric were performed. Multivariate logistic regression models were developed using data from each site separately as the training set in an iterative process with external validation on data from the other site.

For summary statistics, mean (standard deviation) is shown unless otherwise indicated. For associations between vital signs and illnesses, Wald Chi-square and p values are reported, and for modeling, area under receiver operator characteristics curve (ROC AUC) and 95% confidence intervals are reported. The net reclassification improvement (NRI) was also used to compare the performance of the new vital sign models with the HRC index. NRI is a measure of the fraction of cases that are correctly reclassified by a new risk assessment tool compared to an established tool (See Leening M J G, Vedder M M, Witteman J C M, Pencina M J, Steyerberg E W. Net Reclassification Improvement: Computation, Interpretation, and Controversies. Ann Intern Med 2014; 160:122-31). Analyses were performed in MATLAB (MathWorks, Natick Mass.).

Of 1125 VLBW infants admitted to the two NICUs during the study period, vital sign data were available for 1065 (757 in 64 months at UVA and 308 in 18 months at Columbia). The gestational age and birth weight were similar at the two institutions (UVA: 27.6±2.9 weeks and 1003±297 grams; Columbia: 28.5±3.2 weeks and 1030±313, grams). The total number of infant-years' vital sign data available for analysis was 95 and 36 for UVA and Columbia infants.

Among the 1065 infants, there were 123 cases of LOS and 63 cases of NEC with vital sign data available around the time of illness. The mean gestational age and birth weight of infants with LOS or NEC were 25.9 weeks and 817 grams, significantly lower than infants without these illnesses. The organism distribution for the LOS cases was 88 (72%) Gram-positive, 34 (28%) Gram-negative or multiple organisms, and one Candida species. The demographics and organisms for the LOS and NEC cases were similar at the two institutions. The infants with LOS were more likely to be on mechanical ventilation at the time of diagnosis (65/123, 53%) compared to infants with NEC (13/65, 21%), and infants at UVA were more likely to be on mechanical ventilation at the time of LOS or NEC (64/121, 53%) compared to infants at Columbia (14/65, 22%).

The mean, standard deviation and cross-correlation of HR, RR, and SpO2 were analyzed during all times data were available. The total number of hours of data analyzed was 1.15 million (130.9 infant-years), and the breakdown by institution was UVA, 0.84M (95.4 infant-years) and Columbia 0.31M (35.5 infant-years).

FIG. 3 summarizes demographic variables and mean vital signs for the entire NICU stay for all 1065 infants, and vital signs in the 24 hour period before diagnosis of either LOS or NEC. Mean post-menstrual age (PMA) at the time of illness was 30.4 weeks. In univariate analysis, the best predictor of LOS or NEC being diagnosed within 24 hours was PMA. In multivariate analysis adjusting for PMA, cross correlation of HR-SpO2 had the highest ROC area for LOS or NEC (0.733, p<0.001).

FIG. 4 shows means of each vital sign-related parameter in the 2 day period before and after LOS or NEC diagnosis compared to the population mean for all infants for the entire NICU stay (horizontal gray line). Generally, mean HR increased slightly and mean SpO2 decreased slightly around the time of diagnosis. Mean RR did not increase prior to diagnosis but its standard deviation did, which may reflect infants having more fluctuations between tachypnea and apnea. The vital sign parameters changed after diagnosis, possibly related to therapeutic interventions such as increased respiratory support. Of note, changes in vital sign measures in the day prior to illness differed between centers. For example, there was a small, but statistically significant decrease in mean SpO2 and increase in mean HR at UVA and not at Columbia, whereas SD of SpO2 changed before illness at Columbia and not at UVA. Importantly, though, the cross-correlation of HR-SpO2, which measures co-trending of the two vital signs rather than their absolute values, was the best single predictor of illness at both centers.

FIG. 5 shows center-specific vital sign model ability to discriminate infants with impending LOS or NEC. For modeling, the UVA training set consisted of 825,493 hourly measurements with an event rate of 0.0032 and the Columbia training set consisted of 235,458 hourly measurements with an event rate of 0.0035. The contribution of each vital sign to the 9-variable model is represented as a Chi-squared value and corresponding coefficient p value. The performance and confidence intervals of the 9-variable model and a model using the 3 best independent predictors (mean SpO2, SD HR, and cross-correlation HR-SpO2) is shown. The table shows results of training and testing the model at each site separately and combined. The present invention also performed external cross-validation. The UVA 3-variable model had an AUC of 0.754 when tested on Columbia data and the Columbia model had AUC 0.680 tested on UVA data. The 9-variable model had slightly less external validated performance with corresponding AUCs of 0.727 and 0.674.

Figure 6:
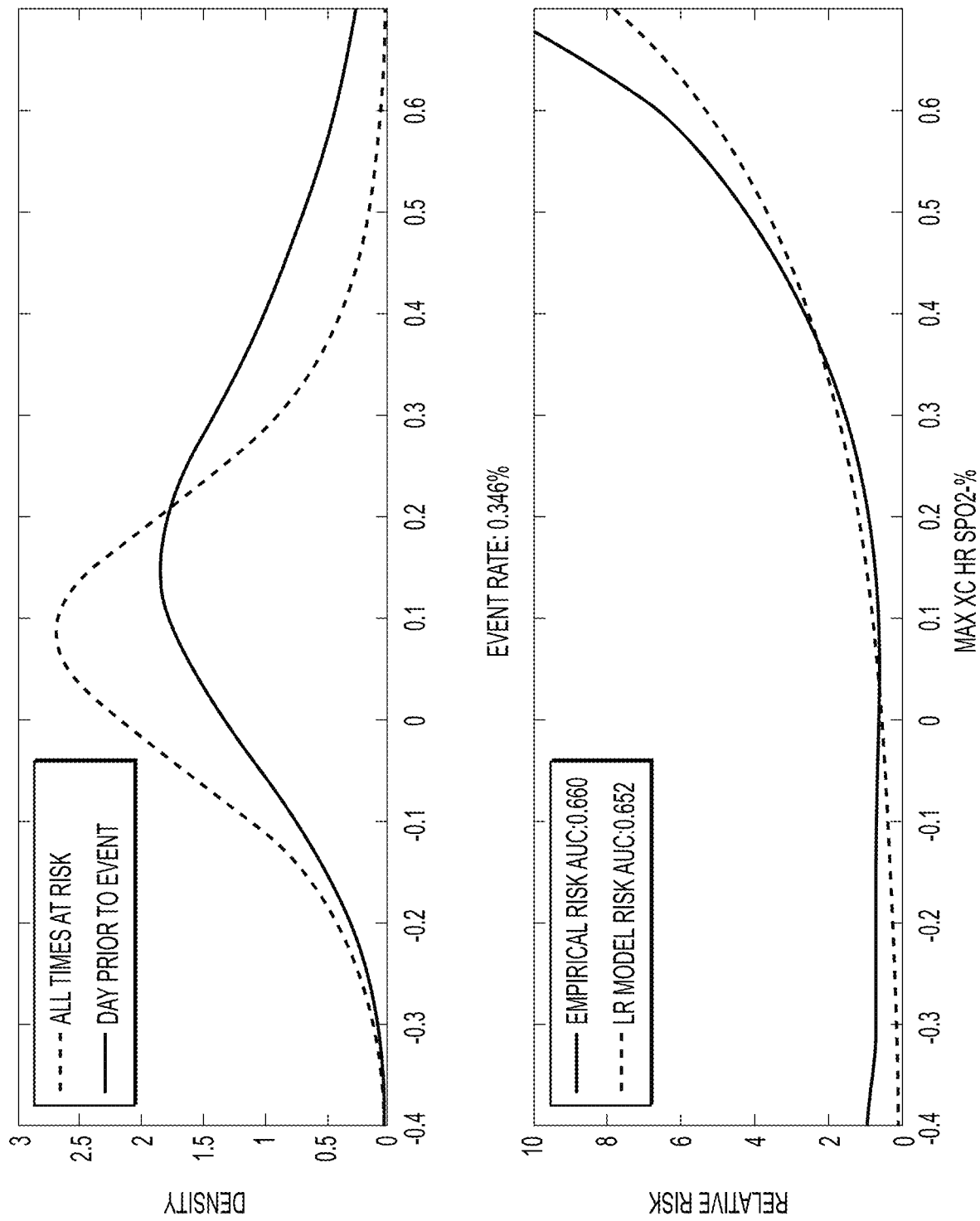
FIG. 6 are graphs of the distribution of cross-correlation of HR-SpO2 measurement skewed toward higher values in the $24^{th}$ period prior to LOS or NEC diagnosis compared to the values of all infants at all times.
Figure 7:
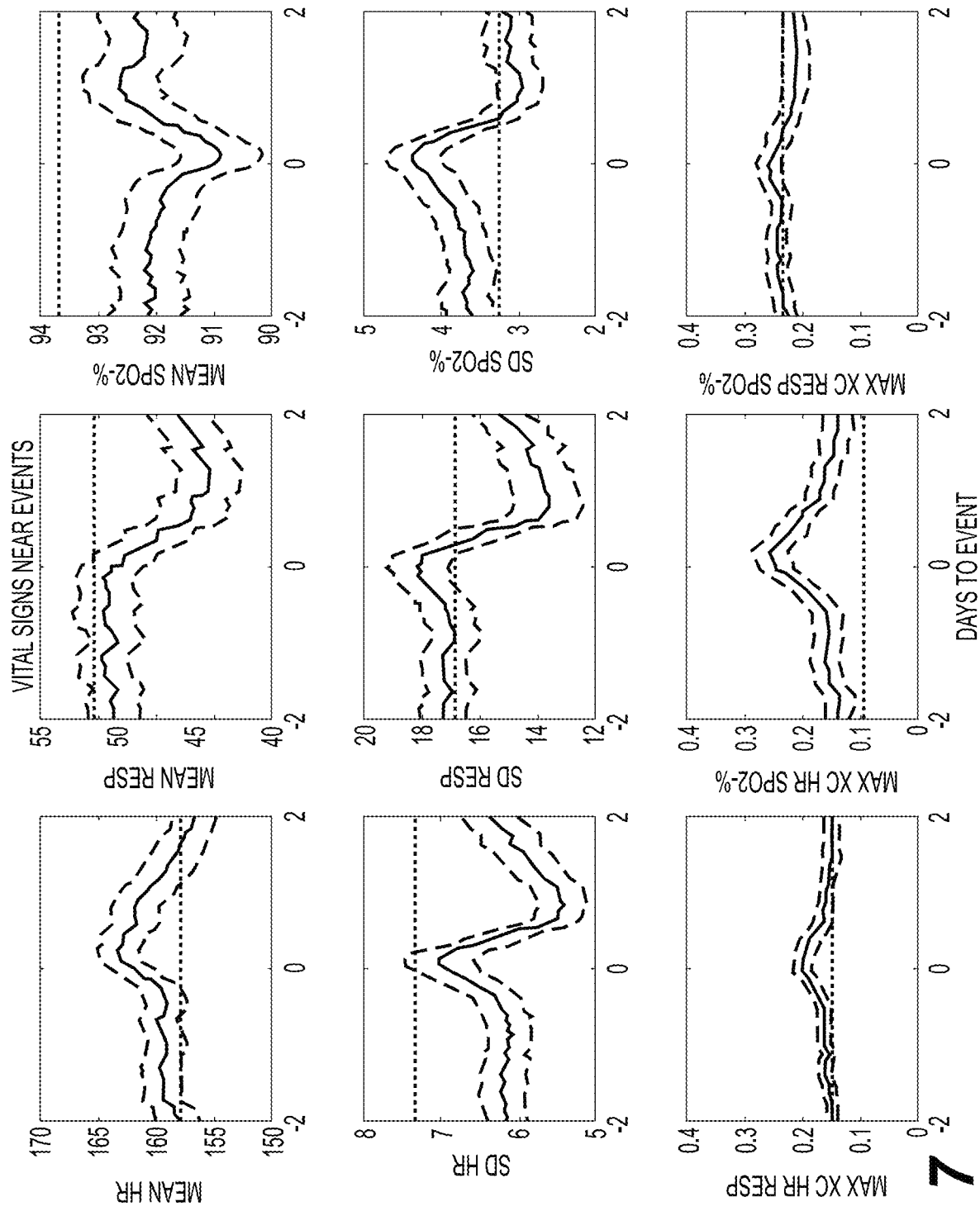
FIG. 7 show graphs of the rise in cross correlation HR-SpO2 being greater in cases of NEC than LOS, and continued to rise after diagnosis.

FIG. 6 shows that the distribution of cross-correlation of HR-SpO2 measurements was skewed toward higher values in the 24 h period prior to LOS or NEC diagnosis compared to the values of all infants at all times. The rise in cross correlation HR-SpO2 was greater in cases of NEC than LOS and continued to rise after diagnosis (FIG. 7). The effect was seen in infants at both institutions (FIG. 8) and in infants on or off mechanical ventilation at the time of diagnosis (See FIGS. 9A-H). Combining LOS and NEC cases and both institutions, mean cross correlation of HR-SpO2 increased from 0.15 in the 24-48 h period prior to diagnosis to 0.21 from 0-24 h prior (p<0.001).

In 33% of the LOS or NEC events (61/186), at least one of the hours in the day prior to the event had an extremely high cross-correlation >0.6 corresponding to the tail of the distribution in FIG. 6. The present invention speculated that, in some cases, this finding represents apnea or periodic breathing with associated decline in HR and SpO2, and the present inventors reviewed respiratory rate, HR, and SpO2 patterns the day prior to illness diagnosis in all cases with very high cross-correlation.

Representative examples are shown. In some cases there was clearly central apnea associated with decline in HR and SpO2 deep enough to be considered "bradycardia/desaturation" by standard definitions (See Finer N N, Higgins R, Kattwinkel J, Martin R J. Summary proceedings from the apnea-of-prematurity group. Pediatrics 2006; 117:S47-51). In others, the concurrent fall and rise in HR, SpO2, and RR were of lower magnitude and duration but higher frequency, suggestive of periodic breathing with entrainment of HR and SpO2.

An HRC index (HeRO) monitor was in use at UVA during the period of study, and scores were available for 620,978 of the hourly measurements used in the UVA vital sign training set. For this subset, the additional value of the parsimonious 3-parameter vital sign model to the HRC index were evaluated using logistic regression models and the net reclassification improvement (NRI) statistic. (12) The AUC on this subset of data for the vital sign model and HRC index alone were 0.684 and 0.707 respectively.

Combining the 3-variable model with the HRC index increased AUC by 0.021 to 0.728 (95% confidence interval 0.010, 0.047 Wald chi-square=22.6, p=0.00001). The Net Reclassification Improvement for the vital sign model was also highly significant with a value of 0.205 (0.113, 0.328). The cross correlation HR-SpO2 by itself also added significantly to the HRC index (Wald chi-square=9.14, p=0.01) with combined AUC of 0.715. This analysis demonstrates the potential of additional vital sign analyses to improve the sensitivity over the established heart rate characteristics index monitor for early detection of LOS and NEC.

The present inventors previously developed a monitor displaying a heart rate characteristics index as an early warning system for sepsis, and in the current study analyzed not only HR, but also respiratory rate and SpO2. The present inventors further expanded the study by analyzing data from a large number of VLBW infants at two institutions and in two illnesses. The major finding is that, while the value of individual vital signs for detection of LOS and NEC differed across institutions, an increase in cross-correlation of HR-SpO2 performed well in both units and added to the HRC index for early detection of illness.

High cross correlation of HR-SpO2 may reflect apnea in infants who are not on mechanical ventilation. An acute increase in central apnea is one of the most common signs of late-onset septicemia in preterm infants in the NICU (See Das A, Shukla S, Rahman N, Gunzler D, Abughali N. Clinical Indicators of Late-Onset Sepsis Workup in Very Low-Birth-Weight Infants in the Neonatal Intensive Care Unit. Am J Perinatol 2016) and apnea is often accompanied by both bradycardia and oxygen desaturation. Periodic breathing, alternating brief apneic pauses and breaths, is normal in neonates and sometimes associated with decline in HR and SpO2. Preclinical studies indicate that cytokines and prostaglandins released as part of the systemic inflammatory response are responsible for emergence of immature breathing patterns during illness (See Hofstetter A O, Saha S, Siljehav V, Jakobsson P-J, Herlenius E. The induced prostaglandin E2 pathway is a key regulator of the respiratory response to infection and hypoxia in neonates. Proc Natl Acad Sci USA 2007; 104:9894-9; and Balan K V., Kc P, Hoxha Z, Mayer C A, Wilson C G, Martin R J. Vagal afferents modulate cytokine-mediated respiratory control at the neonatal medulla oblongata. Respir Physiol Neurobiol 2011; 178:458-64) and the present inventors have previously reported that some preterm infants exhibit an acute increase in periodic breathing or in central "ABDs" (apnea with both bradycardia and desaturation) in the day before they are diagnosed with LOS or NEC (See Patel M, Mohr M, Lake D, et al. Clinical Associations with Immature Breathing in Preterm Infants. Part 2: Periodic Breathing. Pediatr Res 2016; and Fairchild K, Mohr M, Paget-Brown A, et al. Clinical associations of immature breathing in preterm infants: part 1-central apnea. Pediatr Res 2016). Quantitation of central apnea requires storage and analysis of large data files of chest impedance waveforms which is difficult to implement broadly, and in the current study we sought simpler measures using vital signs and their interactions. On reviewing examples of very high cross-correlation of HR-SpO2, it was found that many were clearly associated with decline in breathing rate consistent with central apnea and periodic breathing, and further work is needed to substantiate this association. Interestingly, some infants on mechanical ventilation also had high cross correlation of HR-SpO2 at the time of LOS or NEC diagnosis, indicating that there is more at play in the pathophysiology than central apnea. The present invention speculates that some of this may reflect autonomic nervous system activation or dysfunction, or altered vasoreactivity as part of a systemic inflammatory response.

In order for predictive models to be widely applicable it is important that they be developed and tested at different institutions. It was found small but statistically significant differences in individual vital signs of infants exist at University of Virginia (UVA) and Columbia University (CU), most notably, mean and standard deviation of SpO2. This may be related to differences in clinical management strategies of lung disease or apnea, and may account for the more robust performance of vital sign interactions such as cross-correlation of HR-SpO2 across institutions, since this measure reflects co-trending rather than absolute values of vital signs.

Any new diagnostic or predictive test such as cross correlation of HR-SpO2 should be compared to existing modalities. The HRC index was previously developed by our group as an early warning system for sepsis and is displayed in the UVA NICU. The present inventors found that cross correlation of HR-SpO2 and the 3-vital sign model incorporating mean SpO2, SD HR, and cross correlation of HR-SpO2 had slightly lower ROC area compared to the HRC index and that there was additive value in combining these measures to improve the sensitivity for early detection of LOS and NEC. More work is required to determine whether displaying one or more scores representing multiple vital sign patterns will facilitate earlier detection of illnesses and improve outcomes of infants in the NICU.

Sepsis and NEC continue to contribute a great deal to morbidity and mortality of preterm infants (See Stoll B J, Hansen N I, Bell E F, et al. Trends in Care Practices, Morbidity, and Mortality of Extremely Preterm Neonates, 1993-2012. JAMA 2015; 314:1039-51). Detection and treatment in the early phase of illness, before overt clinical deterioration, is likely to improve outcomes but is difficult due to the subtlety of the early physiologic changes. Analysis of multiple vital signs and their interactions can assist in preclinical detection in some cases, and translating these metrics to real-time bedside displays and testing their impact on outcomes in randomized clinical trials is an essential next step.

In 186 cases of LOS or NEC at UVA and Columbia, mean, standard deviation and cross-correlation of heart rate (HR), respiratory rate (RR), and oxygen saturation (SpO2) are shown 5 days before and after diagnosis. Mean (solid line) and standard deviation (dotted line) are shown. The horizontal dashed line represents the value for all VLBW infants at all times.

Vital sign data was analyzed for cross-correlation of HR-SpO2 for 1065 VLBW infants at all times and around the time of 123 cases of late-onset septicemia (LOS) and 63 cases of NEC. A) For each cross-correlation value, the density of hourly measurements for all 1065 VLBW infants at all times during the NICU stay is shown by the grey dashed line and the number of measurements in the 24 h period prior to illness diagnosis by the black line. B-D) Mean cross-correlation of HR-SpO2 2 days prior to and following diagnosis of illness. Increased cross-correlation occurred in both illnesses (B, LOS solid line, versus NEC dotted line), in both institutions (C, UVA solid line, versus Columbia dotted line), and in infants on or off mechanical ventilation (D, on ventilator solid line, off ventilator dotted line).

Representative one hour tracing of HR and SpO2 (top), and 10 minute tracings of HR, SpO2, and respiratory rate (insets at bottom) are shown for 2 infants in the day prior to diagnosis of illness. A) UVA infant 5 hours prior to diagnosis of sepsis, when cross-correlation of HR-SpO2 was 0.844. There are frequent HR decelerations (solid black line) and concurrent decline in SpO2 (dotted black line), preceded by decline in respiratory rate (solid grey line in bottom inset, note right Y axis for respiratory rate) B) Columbia infant 1.5 hours prior to diagnosis of NEC, when cross-correlation of HR-SpO2 was 0.81. There are repetitive, regular declines in HR and SpO2 associated with decline in respiratory rate.

It should also be appreciated that the exact manner of obtaining vital signs and measuring the levels of one or more biochemical substances and the subsequent analysis can be accomplished by any number of techniques. For example, it may be achieved by the common paradigm whereby vital signs and samples are taken in person and the vital signs samples are analyzed locally or are physically transferred to other facilities where they can be tested and analyzed. However, it may also be achieved by incorporating a "telemedicine" paradigm whereby, at one or more points during the process, information is transferred over a wired or wireless data communications network to a remote location where subsequent analysis or other processing may take place. For example, an aspect of embodiment of the invention may involve electronically transferring the results of vital signs and sample measurement (E.g., bedside vital sign data) over a data communications network to a remote location where subsequent assessment and/or analysis can take place. Such utilization of telecommunications networks may occur during any step in the process and may be utilized at a single or multiple points. Likewise, telecommunications networks may be incorporated into any part of the system.

Furthermore, information can be displayed at any point during the process, or at any point in the system, in any number of ways. For example, readings and data may be received and/or displayed by the user, clinician, physician, technician, patient or the like by hard copy (e.g., paper), visual graphics, audible signals (such as voice or tones, for example), or any combination thereof. Additionally, any measurements, assessment, analysis, secondary information, diagnosis, reading, data, or discussion may be reduced to hard copy (e.g., paper) or computer storage medium at any point during the process (or system).

Figure 10:
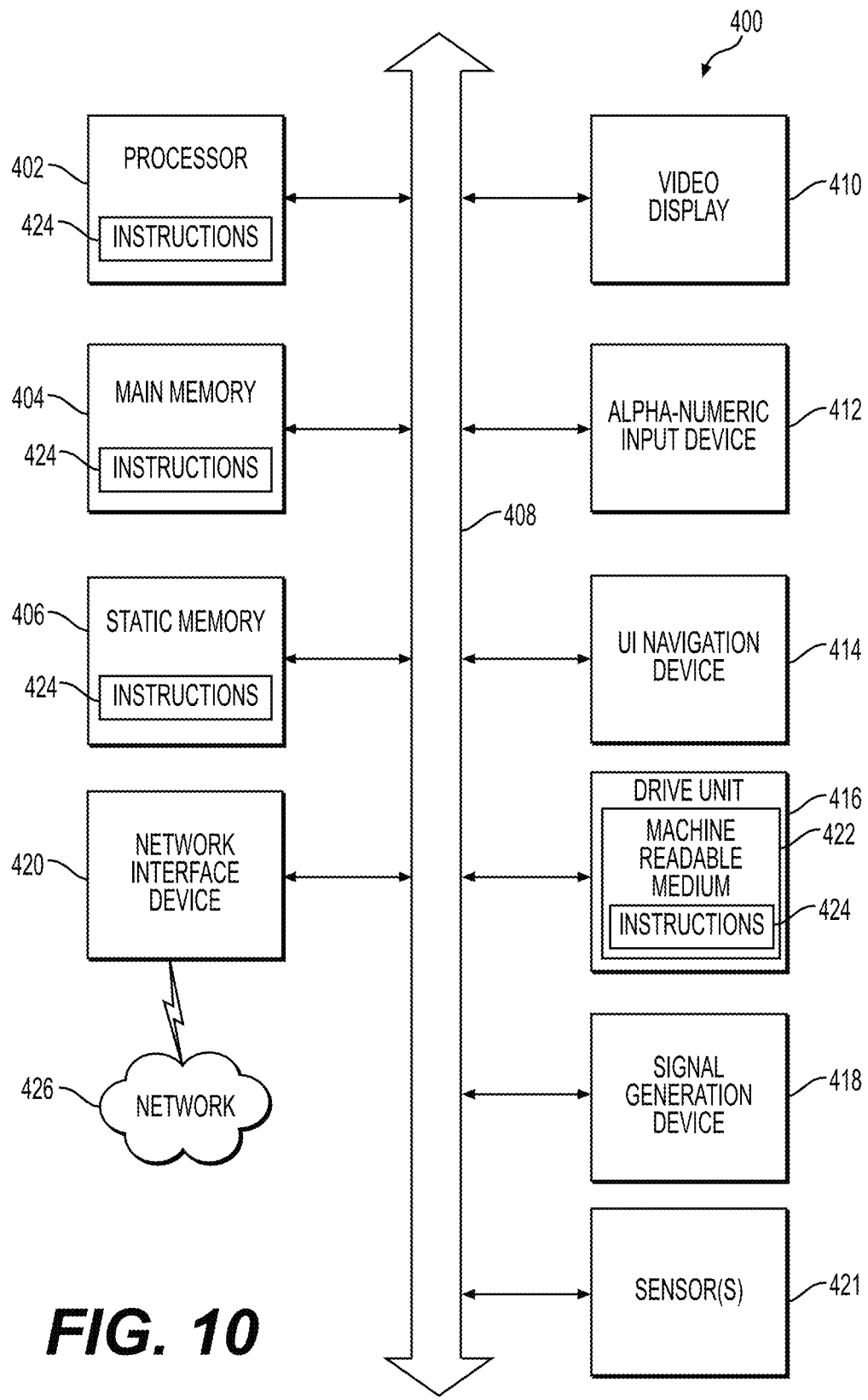
FIG. 10 is a block diagram illustrating an example of a machine upon which one or more aspects of embodiments of the present invention can be implemented.

FIG. 10 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 810, input device 417 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Figure 11:
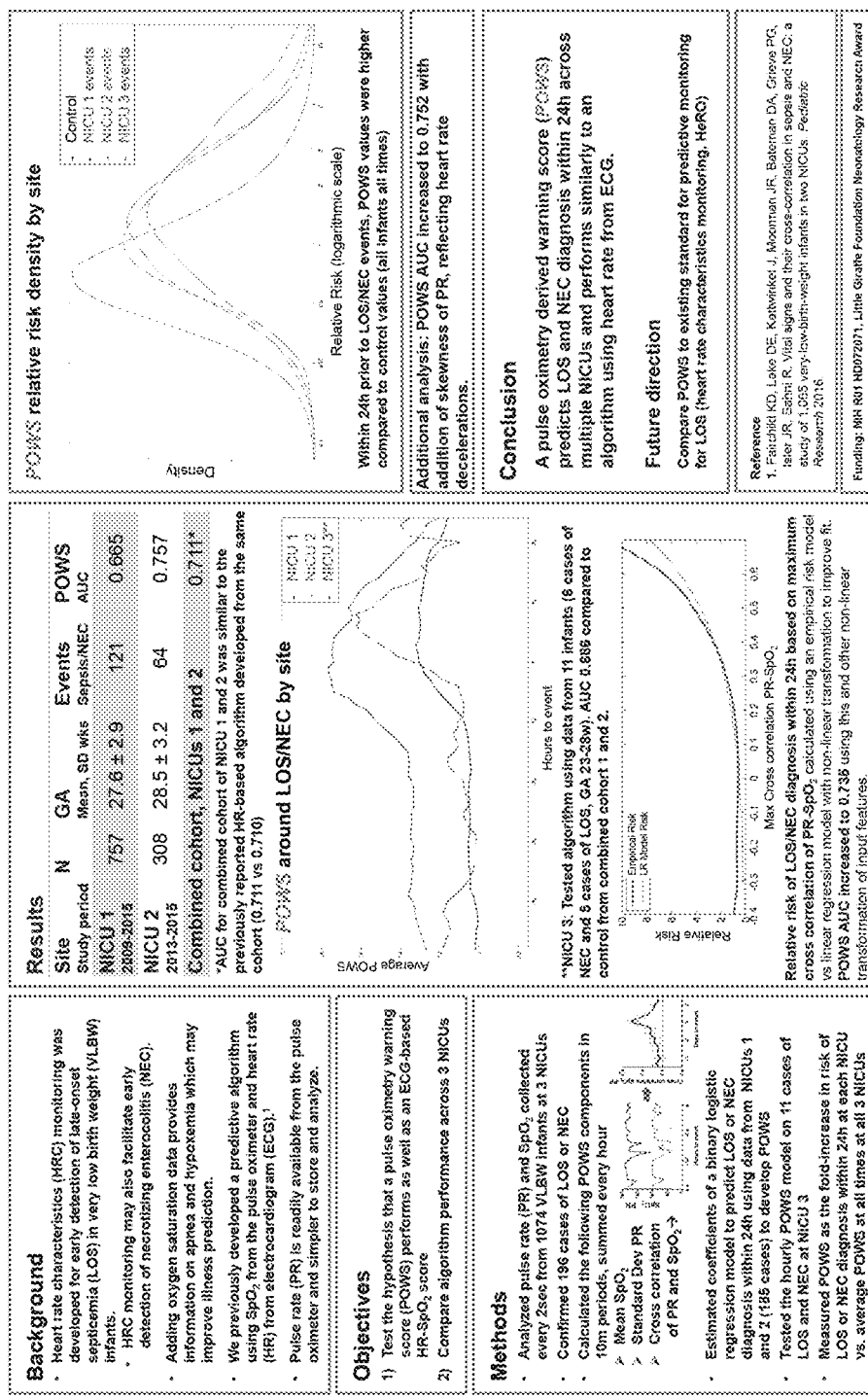
FIG. 11 is a diagram illustrating Pulse Oximetry Warning Score "POWS" for Sepsis and NEC Prediction in VLBW Infants at 3 NICUs.

Pulse Oximetry Warning Scores "Pows" for Sepsis and Nec Prediction I VLBW Infants at Three (3) NICUs The pulse oximetry warning score "POWS" for sepsis and NEC prediction in VLBW infants at three (3) NICUs is shown in FIG. 11.

The details of the background, objectives, and methods are set forth in FIG. 11.

The graph of average POWS verses Hours to event for the three (3) NICUs is shown in FIG. 11. This graph shows the results for predicting sepsis and NEC in VLBW infants. The NICU 3 results are compared to the control from combined cohort 1 and 2.

The graph of Relative Risk verses Max Cross correlation PR-$SpO_2$ is shown in FIG. 11. The relative risk of LOS/NEC diagnosis within 24 h based on maximum cross correlation of PR-$SpO_2$ is calculated using an empirical risk model vs linear regression model with non-linear transformation to improve fit. The POWS AUC increased to 0.735 using this and other non-linear transformation of input features.

The graph of Density verses Relative Risk is shown in FIG. 11. This graph shows that within 24 hours prior to LOS/NEC events, the POWs values were higher compared to control values (all infants all times).

Further, the POWs AUC increased to 0.752 with the addition of skewness of PR, reflecting heart rate decelerations.

In conclusion, pulse oximetry derived warning scores (POWS) predict LOS and NEC diagnosis within 24 hours across the multiple NICUs and performs similarly to an algorithm using heart rate from ECG.

Heart Rate and Oxygen Saturation Cross-Correlation in Preterm Infants: Association with Apnea and Adverse Events The heart rate and oxygen saturation cross-correlation in preterm infants and association with apnea and adverse event is shown in FIG. 12.

Figure 12:
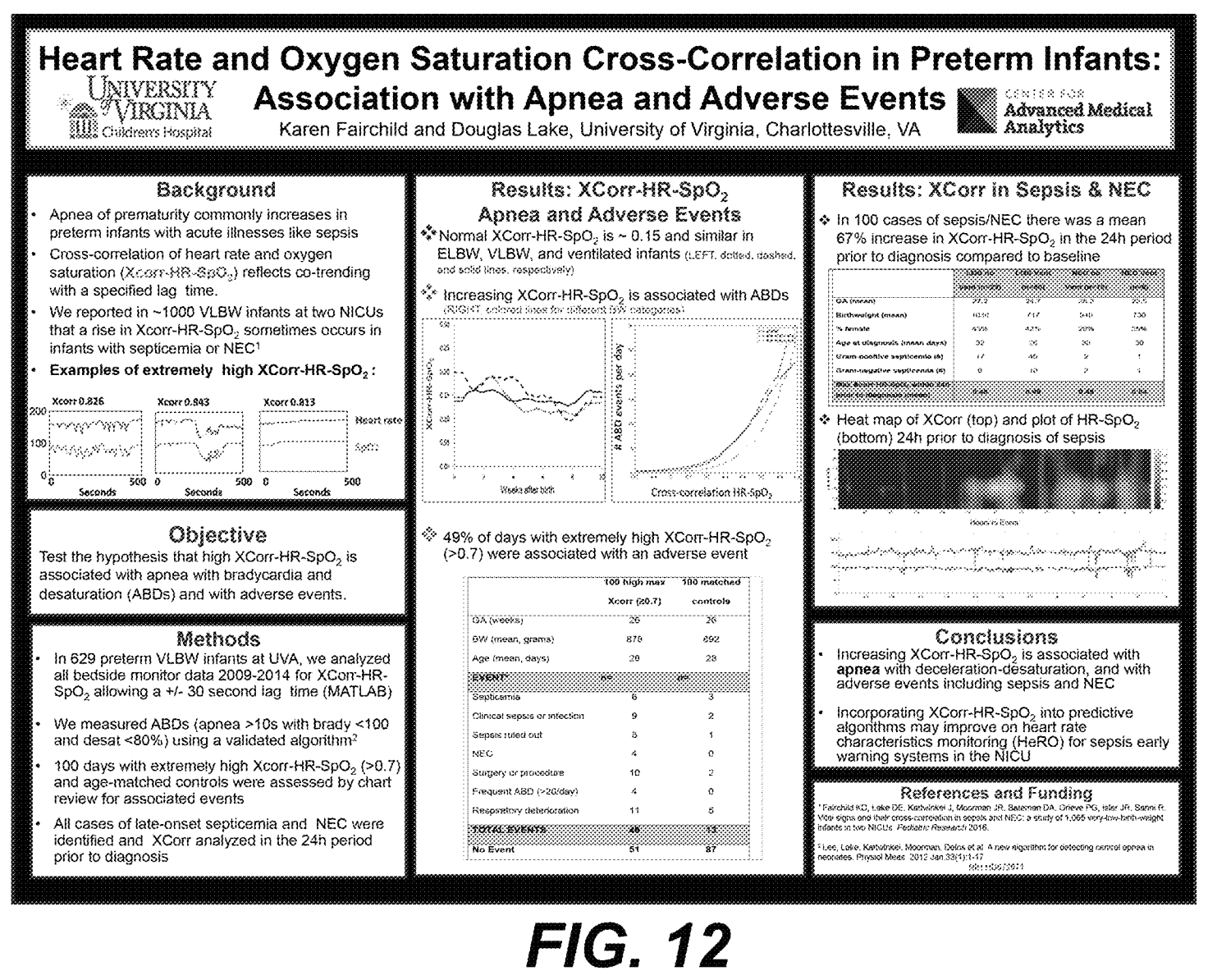

The details of the background, objective, and methods are set forth in FIG. 12.

The graph of XCorr-HR-$SpO_2$ verses Weeks after birth and the graph of # ABD events per day verses XCorr-HR-$SpO_2$ are shown in FIG. 12. Increasing XCorr-HR-$SpO_2$ is associated with ABDs. 49% of days with extremely high XCorr-HR-$SpO_2$ (>0.7) were associated with an adverse event.

The results show in 100 cases of sepsis/NEC, there was a mean 67% increase in XCorr-HR-$SpO_2$ in the 24 hour period prior to diagnosis compared to the baseline. The heat map of XCorr-HR-$SpO_2$ and plot of HR-$SpO_2$ 24 hours prior to diagnosis of sepsis is shown in FIG. 12.

In conclusion, increasing XCorr-HR-$SpO_2$ is associated with apnea with deceleration-desaturation, and with adverse events including sepsis and NEC. Further, incorporating XCorr-HR-$SpO_2$ into predictive algorithms may improve on heart rate characteristics monitoring (HeRO) for sepsis early warning systems in the NICU.

Figure 13:
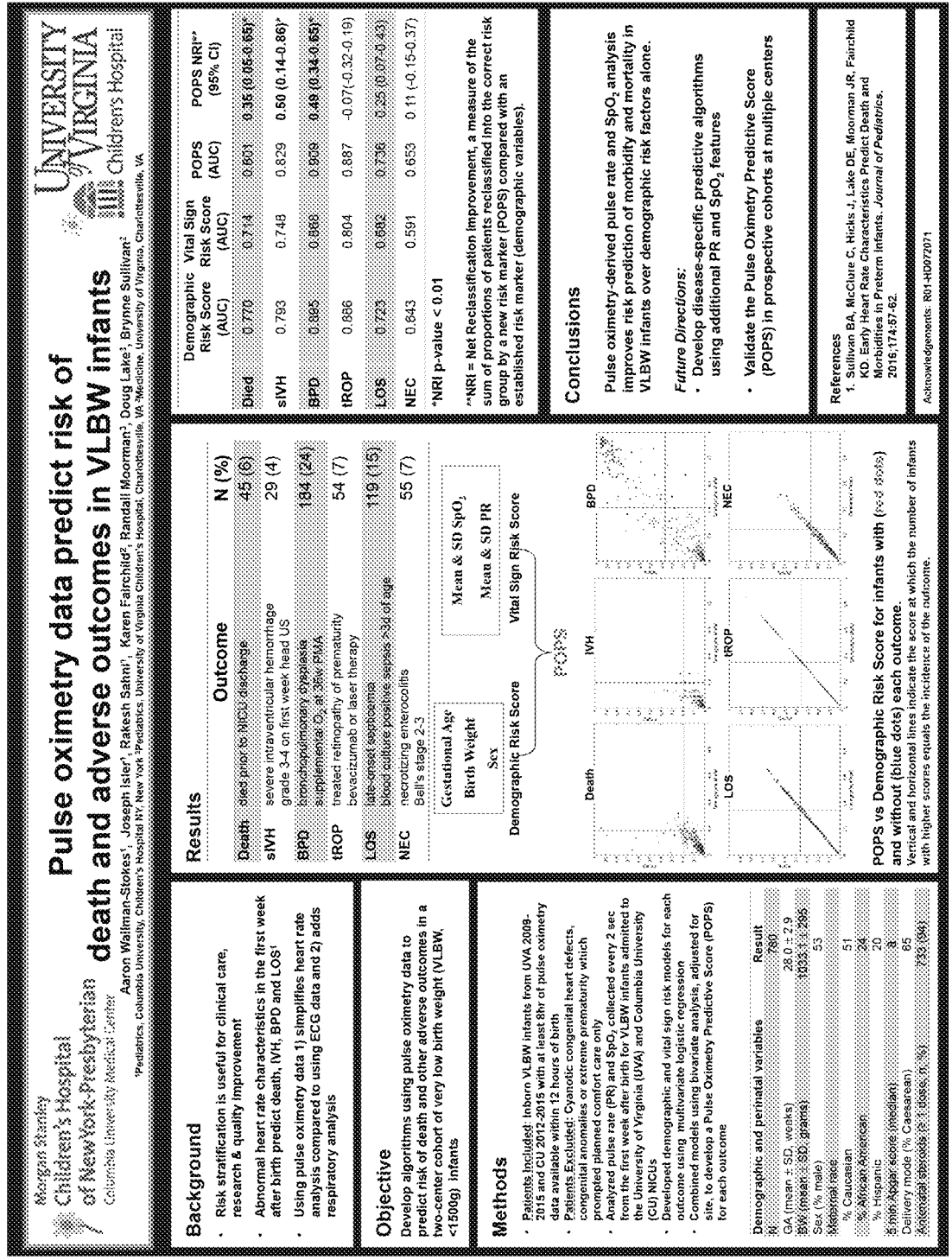
FIG. 13 is a diagram illustrating Pulse oximetry data predict risk of death and adverse outcomes in VLBW infants.

Pulse Oximetry Data Predicting Risk of Death and Adverse Outcomes in VLBW Infants The pulse oximetry data predicting risk of death and adverse outcomes in VLBW infants is shown in FIG. 13.

The details of the background, objective, and methods are shown in FIG. 13.

The results, including death, sIVH, BPD, tROP, LOS, and NEC are shown in FIG. 13.

In conclusion, pulse oximetry-derived pulse rate and $SpO_2$ analysis improves risk prediction of morbidity and mortality in VLBW infants over demographic risk factors alone.

Definitions

The definitions for acronyms used through the application are as follows:
ABD apnea with both bradycardia and desaturation
API application program interface
ASIC application-specific integrated circuit
AUC area under the curve
BPD bronchopulmonary dysplasia
BW birth weight
CD-ROM compact disk read-only memory
COLUMBIA Columbia University
CPU central processing unit
CU Columbia University
DVD-ROM digital optical disk read-only memory
ECG electrocardiogram
EEPROM electrically erasable programmable read-only memory
EPROM programmable read-only memory
FPGA field programmable gate array
GA gestational age
GPS global positioning system
GPU graphic processing unit
HR heart rate
HTTP hypertext transfer protocol
IP internet protocol
HRC heart rate characteristics (index)
IVH intraventricular hemorrhage
LAN local area network
LOS late-onset septicemia
NEC necrotizing enterocolitis
NICU neonatal Intensive Care Unit
NIH National Institute of Health
NRI net reclassification improvement
PC personal computer
PDA personal digital assistant
POPS pulse oximetry predictive scores
POTS plain old telephone service
ROC receiver operating characteristic
ROP retinopathy of prematurity
RR respiratory rate
SD standard deviation
SpO2 peripheral capillary oxygen saturation
STB set-top box
TCP transmission control protocol
UDP user datagram protocol
UI user interface
UVA University of Virginia
VLBW very low birth weight (infants)
WAN wide area network In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

The invention claimed is:

1. A method for generating pulse oximetry predictive scores (POPS) for predicting occurrence of predetermined pathologies in a preterm infant, the method comprising:
   receiving in at least one processor Heart Rate (HR) and oxygen saturation (SpO2) data collected from the preterm infant with a pulse oximetry sensor;
   calculating by said at least one processor mean and standard deviation of HR and SpO2, cross-correlation of HR and SpO2, HR decelerations, HR and SpO2 entropy, hypoxia and hyperoxia from said received HR and SpO2 data, wherein the calculations are made over different time periods specific to a predetermined pathology;
   generating by said at least one processor pulse oximetry predictive scores with a predictive algorithm which incorporates a cross-correlation of HR and SpO2 based on archived pulse oximetry data of multiple preterm infants to analyze the calculated data;
   outputting said generated pulse oximetry predictive scores (POPS) on an output device to a user;
   predicting the predetermined pathology of said preterm infant based on the generated POPS, wherein the pathology includes at least one of intraventricular hemorrhage (IVH), late-onset sepsis (LOS), necrotizing enterocolitis (NEC), bronchopulmonary dysplasia (BPD), or retinopathy of prematurity (ROP); and
   based on the outputted POPS, performing an action selected from the group of:
   identifying said preterm infant as a highest risk infant and performing additional surveillance of or therapeutic intervention on said preterm infant;
   identifying said preterm infant for participation in a clinical trial based on a risk profile associated with said POPS; and
   treating said preterm infant for said pathology.

2. The method according to claim 1, wherein the time periods are based on death or intraventricular hemorrhage (IVH) at first 24 hour or shorter time periods, after birth.

3. The method according to claim 1, wherein the time periods are based on sepsis or necrotizing enterocolitis (NEC) at 2 days leading up to clinical diagnosis, including increase over patient baseline or increase over population normal.

4. The method according to claim 1, wherein the time periods are based on bronchopulmonary dysplasia (BPD) or retinopathy of prematurity (ROP) at first day, week, or month.

5. The method according to claim 1, wherein the time periods are based on prolonged Neonatal Intensive Care Unit (NICU) stay at first day, week, or month.

6. The method according to claim 1, wherein the predictive algorithm additionally incorporates gestational age, birth weight, and post-menstrual age.

7. The method according to claim 1, wherein the data collected from the preterm infant further includes specific laboratory values, including white blood cell count, hematocrit, and C-reactive protein.

8. The method according to claim 7, wherein the predictive algorithm additionally incorporates standard demographic risk factors to determine risk of early or late death or prolonged Neonatal Intensive Care Unit (NICU) stay.

9. The method according to claim 1, including monitoring changes in cardiorespiratory changes occurring in the preterm infant with systemic inflammation related to late-onset septicemia (LOS) or necrotizing enterocolitis (NEC), and alerting clinicians before overt signs of illness emerges.

10. The method according to claim 9, including monitoring respiratory rate (RR), heart rate (HR), and oxygen saturation (SpO2) of the preterm infant.

11. The method according to claim 1, including monitoring changes in vital sign patterns of the preterm infant.

12. The method according to claim 11, wherein monitoring data is collected using a server.

13. The method according to claim 12, wherein the monitoring data includes respiration rate (RR) derived from a chest impedance signal, heart rate (HR) derived from an electrocardiogram (ECG) signal, and oxygen saturation (SpO2) derived from a pulse oximeter, and the monitoring data is collected every 2 seconds.

14. The method according to claim 13, wherein maximum cross-correlation between two vital sign signals is calculated over ten-minute windows by first standardizing each signal and then using a MATLAB® function XCORR, with a lag time of −30 to +30 seconds.

* * * * *